(12) United States Patent
Kaemmerer et al.

(10) Patent No.: US 11,040,205 B2
(45) Date of Patent: *Jun. 22, 2021

(54) THERAPY PROGRAM SELECTION FOR ELECTRICAL STIMULATION THERAPY BASED ON A VOLUME OF TISSUE ACTIVATION

(71) Applicant: Medtronic, Inc., Minneapolis, MN (US)

(72) Inventors: William F. Kaemmerer, Edina, MN (US); Maciej T. Lazarewicz, Maple Grove, MN (US); Gabriela C. Molnar, Blaine, MN (US); Ashutosh Chaturvedi, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 255 days.

This patent is subject to a terminal disclaimer.

(21) Appl. No.: 16/228,972

(22) Filed: Dec. 21, 2018

(65) Prior Publication Data

US 2019/0111266 A1 Apr. 18, 2019

Related U.S. Application Data

(63) Continuation of application No. 15/044,795, filed on Feb. 16, 2016, now Pat. No. 10,188,863.

(Continued)

(51) Int. Cl.
*A61N 1/36* (2006.01)
*G16H 50/30* (2018.01)
(Continued)

(52) U.S. Cl.
CPC ....... *A61N 1/3614* (2017.08); *A61N 1/36185* (2013.01); *A61N 1/37247* (2013.01);
(Continued)

(58) Field of Classification Search
CPC ............ A61N 1/36185; A61N 1/37247; A61N 1/3605; A61N 1/36082; A61N 1/36182
See application file for complete search history.

(56) References Cited

U.S. PATENT DOCUMENTS 7,822,483 B2 10/2010 Stone et al.
8,180,445 B1 5/2012 Moffitt et al.
(Continued)

FOREIGN PATENT DOCUMENTS

CA 2745435 A1 6/2010
CN 102698360 A 10/2012
(Continued)

OTHER PUBLICATIONS

International Preliminary Report on Patentability from International Application No. PCT/US2016/018255, dated Sep. 8, 2017, 9 pp.

(Continued)

*Primary Examiner* — George R Evanisko
(74) *Attorney, Agent, or Firm* — Shumaker & Sieffert, P.A.

(57) ABSTRACT

In some examples, a processor of a system evaluates a therapy program based on a score determined based on a volume of tissue expected to be activated ("VTA") by therapy delivery according to the therapy program. The score may be determined using a three-dimensional (3D) grid comprising a plurality of voxels that are each assigned a value. The processor may register the VTA with the 3D grid and determine the score for the therapy program based on the values assigned to voxels with which the VTA overlaps. One or more therapy programs for electrical stimulation therapy (e.g., deep brain stimulation) may be selected based on the scores determined based on the 3D grid.

19 Claims, 11 Drawing Sheets

Related U.S. Application Data

(60) Provisional application No. 62/121,295, filed on Feb. 26, 2015.

(51) Int. Cl.

| | | |
|---|---|---|
| *G16H 20/30* | (2018.01) | |
| *A61N 1/372* | (2006.01) | |
| *G06F 19/00* | (2018.01) | |
| *G16H 20/40* | (2018.01) | |
| *G16H 50/50* | (2018.01) | |

(52) U.S. Cl.
CPC ............ *G06F 19/00* (2013.01); *G16H 20/30* (2018.01); *G16H 20/40* (2018.01); *G16H 50/30* (2018.01); *A61N 1/3605* (2013.01); *A61N 1/36082* (2013.01); *A61N 1/36128* (2013.01); *A61N 1/36182* (2013.01); *G16H 50/50* (2018.01)

(56) References Cited

U.S. PATENT DOCUMENTS

| | | |
|---|---|---|
| 9,764,136 B2 * | 9/2017 | McIntyre ............... G16H 50/20 |
| 10,188,863 B2 * | 1/2019 | Kaemmerer ....... A61N 1/37247 |
| 2006/0017749 A1 | 1/2006 | McIntyre et al. |
| 2007/0083104 A1 | 4/2007 | Butson et al. |
| 2007/0225674 A1 | 9/2007 | Molnar et al. |
| 2008/0269836 A1 | 10/2008 | Foffani et al. |
| 2009/0118610 A1 | 5/2009 | Karmarkar et al. |
| 2009/0287271 A1 | 11/2009 | Blum et al. |
| 2010/0042011 A1 | 2/2010 | Doidge et al. |
| 2010/0214318 A1 | 8/2010 | Pradeep et al. |
| 2010/0241020 A1 | 9/2010 | Zaidel et al. |
| 2010/0249538 A1 | 9/2010 | Pradeep et al. |
| 2011/0125078 A1 | 5/2011 | Denison et al. |
| 2011/0144715 A1 | 6/2011 | Molnar et al. |
| 2011/0184489 A1 | 7/2011 | Nicolelis et al. |
| 2011/0307030 A1 | 12/2011 | John |
| 2011/0313236 A1 | 12/2011 | Valente et al. |
| 2012/0116211 A1 | 5/2012 | McIntyre et al. |
| 2012/0116475 A1 | 5/2012 | Nelson et al. |
| 2012/0197611 A1 | 8/2012 | Butson et al. |
| 2013/0030276 A1 | 1/2013 | McIntyre et al. |
| 2013/0053722 A1 | 2/2013 | Carlson et al. |
| 2013/0150922 A1 | 6/2013 | Butson |
| 2013/0172716 A1 | 7/2013 | Lozano et al. |
| 2013/0197605 A1 | 8/2013 | Carlson et al. |
| 2013/0268019 A1 | 10/2013 | Gupta et al. |
| 2013/0289380 A1 | 10/2013 | Molnar et al. |
| 2014/0135870 A1 | 5/2014 | Carlson et al. |
| 2016/0220850 A1 | 8/2016 | Tyler |

FOREIGN PATENT DOCUMENTS

| | | |
|---|---|---|
| CN | 102791332 A | 11/2012 |
| WO | 2010065888 A3 | 6/2010 |
| WO | 2013173778 A1 | 11/2013 |

OTHER PUBLICATIONS

Astrom, "Modelling, Simulation, and Visualization of Deep Brain Stimulation," Linkoping University, Aug. 18, 2011, 100 pp.

Carlson et al., "Deep Brain Stimulation Does Not Silence Neurons in Subthalamic Nucleus in Parkinson's Patients," J. Neurophysiol, Dec. 2, 2009, 16 pp.

International Search Report and Written Opinion from International Application No. PCT/US2016/018255, dated Jun. 3, 2016, 14 pp.

Prosecution History from Appl. No. 15/044,795, dated Nov. 8, 2017 through Sep. 14, 2018, 105 pp.

First Office Action and Search Report, and English translation thereof, from counterpart Chinese Application No. 201680012541.3, dated Jan. 3, 2020, 10 pp.

Notification of Grant, and translation thereof, dated Mar. 15, 2021, from counterpart Chinese Application No. 20168001254.1 3 pp.

* cited by examiner

THERAPY PROGRAM SELECTION FOR ELECTRICAL STIMULATION THERAPY BASED ON A VOLUME OF TISSUE ACTIVATION

This application is a continuation of U.S. patent application Ser. No. 15/044,795, filed Feb. 16, 2016, which claims the benefit of U.S. Provisional Patent Application No. 62/121,295, filed on Feb. 26, 2015, and entitled "THERAPY PROGRAM SELECTION FOR ELECTRICAL STIMULATION THERAPY BASED ON A VOLUME OF TISSUE ACTIVATION," the entire contents of which is incorporated herein by reference.

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation. In some therapy systems, an implantable electrical stimulator delivers electrical therapy to a target tissue site within a patient with the aid of one or more electrodes, which may be deployed by medical leads, on a housing of the electrical stimulator, or both.

During a programming session, which may occur during implant of the medical device, during a trial session, or during an in-clinic or remote follow-up session after the medical device is implanted in a patient, a clinician may generate one or more therapy programs (also referred to as therapy parameter sets) that provide efficacious therapy to the patient, where each therapy program may define values for a set of therapy parameters. A medical device may deliver therapy to the patient according to one or more stored therapy programs. In the case of electrical stimulation, the therapy parameters may define characteristics of the electrical stimulation waveform to be delivered.

SUMMARY

The disclosure describes example devices, systems, and methods for determining one or more therapy programs for electrical stimulation therapy based on a volume of tissue expected to be activated by electrical stimulation delivered according to the therapy program. The electrical stimulation therapy may be, for example, deep brain stimulation ("DBS") or electrical stimulation of the brainstem, spinal cord, or another tissue of the central nervous system. The volume of tissue expected to be activated by the electrical stimulation may also be referred to as a volume of tissue activation ("VTA"). In some examples, a processor of a system evaluates a therapy program based on a score determined using a VTA generated based on the therapy program. The therapy program may define values for a plurality of therapy parameters. The score may be determined using a three-dimensional (3D) grid comprising a plurality of voxels that are each assigned a value. The processor may register the VTA with the 3D grid and determine the score for the therapy program based on the values assigned to voxels with which the VTA overlaps. For example, the score may be the sum of the values assigned to the voxels. The processor may select one or more therapy programs based on the scores determined in this manner based on the 3D grid.

In some examples, the values assigned to the voxels are determined based on one or more frequency domain characteristics of respective bioelectrical brain signals sensed during delivery of electrical stimulation according to one or more test therapy programs. For example, a processor may determine a VTA expected to result from delivery of electrical stimulation according to a test therapy program, register the VTA to a 3D grid, determine a frequency domain characteristic of a bioelectrical brain signal sensed during delivery of electrical stimulation according to the test therapy program, and assign at least one voxel of the 3D grid overlapping with the VTA a value based on the frequency domain characteristic of the bioelectrical brain signal.

In examples in which a plurality of test therapy programs are used to determine the values assigned to the voxels of the 3D grid, the processor may determine the VTAs expected to result from delivery of electrical stimulation according to each test therapy program of a plurality of test therapy programs, register the VTAs to a 3D grid, and determine, for each test therapy program, a frequency domain characteristic of a bioelectrical brain signal sensed during delivery of electrical stimulation according to the test therapy program. The frequency domain characteristic for each therapy program may be associated with the VTAs generated based on the respective therapy program. The processor may then assign at least some voxels of the 3D grid values that are based on the frequency domain characteristics associated with the VTAs with which the voxels overlap.

In one example, the disclosure is directed to a method comprising determining, by a processor, values for a plurality of voxels of a three-dimensional grid, wherein determining the values comprises determining a VTA expected to result from delivery of electrical stimulation by a medical device according to a therapy program; registering the VTA to the three-dimensional grid; determining a frequency domain characteristic of a bioelectrical brain signal of a patient sensed during delivery of electrical stimulation to the patient by the medical device according to the therapy program; and determining a value for at least one of the voxels overlapping with the VTA based on the frequency domain characteristic of the bioelectrical brain signal. The method may further comprise controlling or otherwise adjusting electrical stimulation therapy to a patient based on the values of the voxels.

In another example, the disclosure is directed to a system comprising a memory that stores a three-dimensional grid comprising a plurality of voxel, and a processor configured to determine values for the plurality of voxels by at least determining a VTA expected to result from delivery of electrical stimulation by a medical device according to a therapy program, registering the VTA to the three-dimensional grid, determining a frequency domain characteristic of a bioelectrical brain signal of a patient sensed during delivery of electrical stimulation by the medical device to the patient according to the therapy program, and determining a value for at least one voxel overlapping with the VTA based on the frequency domain characteristic of the bioelectrical brain signal, wherein the processor is further configured to store the determined values in the memory. In some examples, the processor is further configured to control or otherwise adjust electrical stimulation therapy delivered to a patient by a medical device based on the values of the voxels.

In another example, the disclosure is directed to a system comprising means for determining values for a plurality of voxels of a three-dimensional grid, wherein the means for determining the values comprises means for determining a VTA expected to result from delivery of electrical stimulation by a medical device according to a therapy program; means for registering the VTA to the three-dimensional grid; means for determining a frequency domain characteristic of a bioelectrical brain signal of a patient sensed during delivery of electrical stimulation to the patient by the medical device according to the therapy program; and means for determining a value for at least one voxel overlapping with the VTA based on the frequency domain characteristic of the bioelectrical brain signal. In some examples, the system further comprises means for controlling or otherwise adjusting electrical stimulation therapy delivered to a patient by a medical device based on the values of the voxels.

In another example, the disclosure is directed to a computer-readable medium comprising instructions that, when executed, cause a processor to determine values for a plurality of voxels of a three-dimensional grid by at least: determining a VTA expected to result from delivery of electrical stimulation by a medical device according to a therapy program; registering the VTA to the three-dimensional grid; determining a frequency domain characteristic of a bioelectrical brain signal of a patient sensed during delivery of electrical stimulation by the medical device to the patient according to the therapy program; and determining a value for at least one voxel overlapping with the VTA based on the frequency domain characteristic of the bioelectrical brain signal. In some examples, the instructions further cause the processor to control or otherwise adjust electrical stimulation therapy delivered to a patient by a medical device based on the values of the voxels.

In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program.

The details of one or more examples are set forth in the accompanying drawings and the description below. Other features, objects, and advantages will be apparent from the description and drawings, and from the claims.

DETAILED DESCRIPTION

Figure 1:
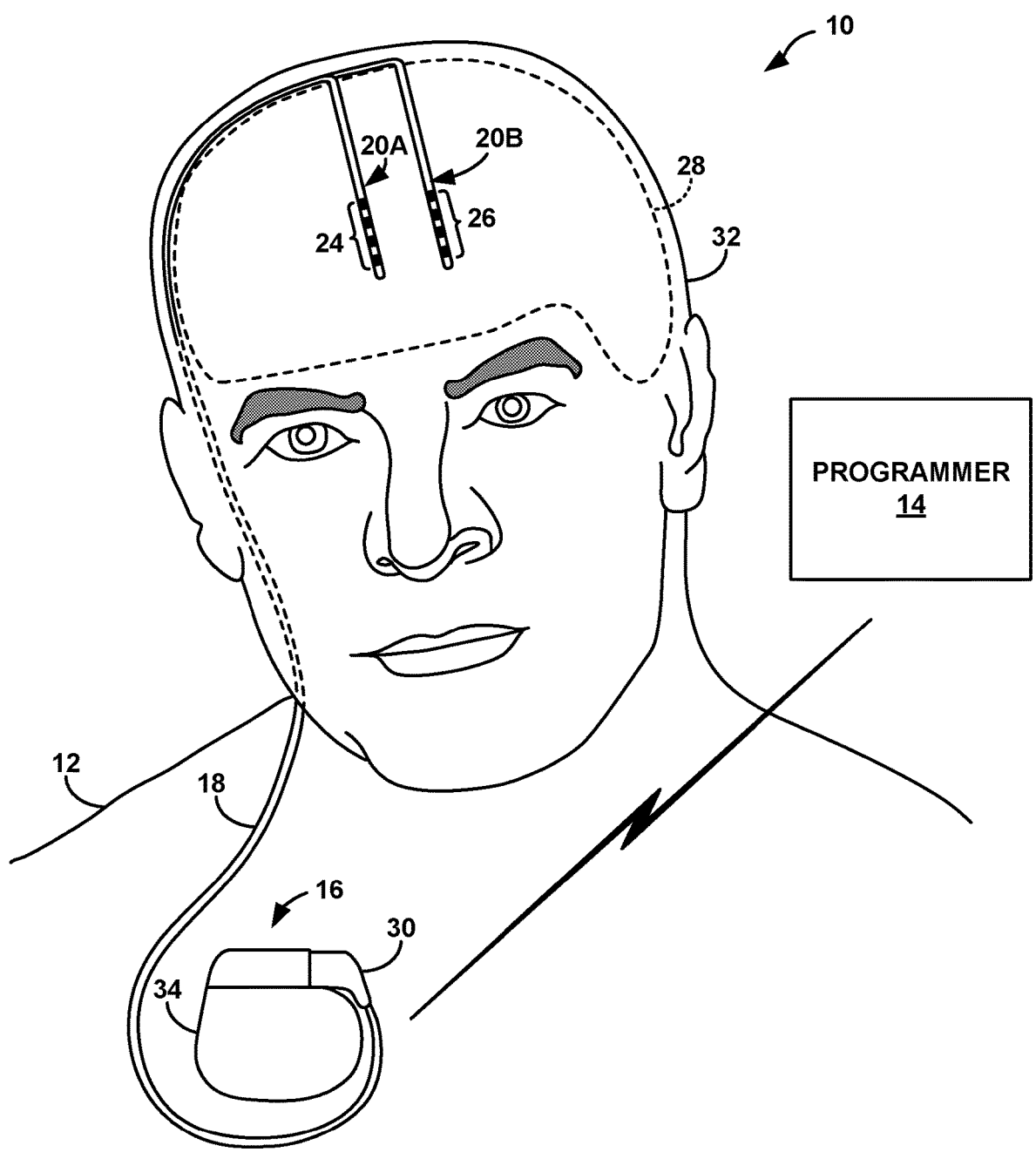
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example devices, systems, and methods for determining one or more therapy programs that may provide efficacious DBS to a patient, where the determination is made based on a volume of tissue expected to be activated ("VTA") by electrical stimulation delivered by a medical device via each of the one or more therapy programs. A therapy program may define, for example, values for one or more electrical stimulation parameters (e.g., frequency, current or voltage amplitude, and pulse width in the case of electrical stimulation pulses), an electrode combination (one or more electrodes selected to deliver electrical stimulation and the respective polarities), or both one or more electrical stimulation parameter values and the electrode combination. The electrodes selected for the combination may be used to steer an electrical field relative to a lead to target a particular therapy site, e.g., in examples in which the lead includes electrodes positioned in various locations around the circumference of the lead.

In some examples, tissue may be "activated" when electrical stimulation delivered by a medical device causes an action potential to propagate along a neuron of the tissue, which may indicate that the transmembrane potential of the neuron reached a particular level, such as a potential greater than 0 millivolts (mV). A VTA may be determined for a particular therapy program (also referred to herein as a "set of electrical stimulation parameter values") using a modeling algorithm that is based on characteristics of the tissue of the patient proximate to the one or more electrodes with which the medical device delivers the electrical stimulation. In this way, the VTA may be estimated.

In some examples, VTAs are determined for one or more therapy programs, and the one or more therapy programs are evaluated based on scores determined based on the respective VTAs. For each therapy program, the score may be determined based on values assigned to voxels of a 3D grid with which the respective VTA overlaps.

In some examples, the values assigned to at least some voxels of the 3D grid are determined based on one or more frequency domain characteristics of respective bioelectrical signals sensed during delivery of electrical stimulation according to respective test therapy programs. For example, a processor may determine the VTAs expected to result from delivery of electrical stimulation according to each test therapy program of a plurality of test therapy programs, register the VTAs to a 3D grid, and determine, for each test therapy program, a frequency domain characteristic of a bioelectrical brain signal sensed during delivery of electrical stimulation according to the test therapy program (e.g., simultaneously with the delivery of electrical stimulation to the patient). The frequency domain characteristic for each test therapy program may be associated with the VTAs generated based on the respective test therapy program. The processor may then assign at least some voxels of the 3D grid a value based on the frequency domain characteristics associated with the VTAs with which the voxels overlap.

For example, in some examples, if a voxel overlaps with only one VTA, then the processor may assign the voxel a value based on the frequency domain characteristic associated with the VTA. As another example, in some examples, if a voxel overlaps with a plurality of the VTAs, then the processor may assign the voxel a value that is based on a maximum change in the frequency domain characteristics associated with the plurality of VTAs relative to a baseline value, a minimum or maximum value of the frequency domain characteristics, an average value of the frequency domain characteristics, a median value of the frequency domain characteristics, or another value that is based on the frequency domain characteristics associated with the plurality of VTAs.

In some examples, the frequency domain characteristic is a power level in a frequency band of interest of the bioelectrical brain signal. In another example, the frequency domain characteristic is the change in the power level in a frequency band of interest of the bioelectrical brain signal relative to a baseline power level. In some examples, the baseline power level may represent a baseline state of the patient, when the patient is not receiving any therapy for the patient condition that the electrical stimulation therapy is expected to help treat. The baseline power level can be, for example, the power level in the frequency band of interest of a bioelectrical brain signal sensed prior to delivery of therapy according to the therapy program, or prior to the delivery of any electrical stimulation therapy to the patient. In other examples, the baseline power level may not be determined based on a patient-specific parameter, but, rather, may be selected by a clinician based on the clinician knowledge or another factor.

The frequency domain characteristic can be determined based on, for example, a spectral analysis of a bioelectrical brain signal. The spectral analysis may indicate the distribution over frequency of the power contained in a signal, based on a finite set of data. Different frequency bands of a bioelectrical brain signal are associated with different activity in the brain of a patient. One example of the frequency bands is shown in Table 1 below:

TABLE 1

| Frequency (f) Band Hertz (Hz) | Frequency Information |
|---|---|
| f <3 Hz | δ (delta frequency band) |
| 3 Hz ≤ f ≤ 8 Hz | θ (theta frequency band) |
| 8 Hz ≤ f ≤ 12 Hz | α (alpha frequency band) |
| 12 Hz ≤ f ≤ 30 Hz | β (beta frequency band) |
| 30 Hz ≤ f ≤ 100 Hz | γ (gamma frequency band) |
| 100 Hz ≤ f ≤ 200 Hz | high γ (high gamma frequency band) |

It is believed that some frequency bands of a bioelectrical brain signal may be more revealing of a patient state (e.g., for purposes of assessing the efficacy of therapy delivery) than other frequency bands. As a result, the one or more frequency bands of interest that are indicative of the efficacy of therapy delivery may change depending on the patient condition. For example, in the case of Parkinson's disease, the frequency domain of interest may be the beta band sensed in the basal ganglia of the brain of the patient.

The determined voxel values may be used to evaluate any given therapy program, alone or in combination with other factors, such as clinician knowledge of desired targets (e.g., anatomical structures of the brain or specific portions of the anatomical structures associated with therapeutic effects) and undesired targets (e.g., anatomical structures of the brain or specific portions of the anatomical structures associated with side effects).

By using the voxel values determined based on the actual effects of DBS on the patient to score one or more therapy programs, the physiologic information of the patient may be used to evaluate the one or more therapy programs. Factoring in the patient-specific physiologic information for the patient when programming a medical device may be help drive a more efficient programming process, e.g., when compared to a process in which a clinician manually selects therapy parameter values or electrode combinations based on intuition or some idiosyncratic methodology.

While deep brain stimulation ("DBS") and bioelectrical brain signals are primarily referred to throughout the disclosure, the devices, systems, and techniques may be used with other types of electrical stimulation therapy, such as electrical stimulation of the brainstem, spinal cord, or another tissue of the central nervous system.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively, alone or in combination with an electrode provided by outer housing 34 of IMD 16.

In the example shown in FIG. 1, therapy system 10 may be referred to as a DBS system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. Frequency bands of therapeutic interest in cortical stimulation therapy may include the theta band, and the gamma band.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post traumatic stress disorder, dysthymic disorder, and obsessive compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12. Therapy systems configured for treatment of other patient conditions via delivery of therapy to brain 28 can also be used in accordance with the techniques for determining one or more therapeutic windows disclosed herein. In addition, Therapy systems configured for treatment of other patient conditions via delivery of electrical stimulation to other tissue sites within patient 12 and not within brain 28.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate to the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16, along the neck of patient 12 and through the cranium of patient 12 to access brain 28. IMD 16 can be constructed of a biocompatible material that resists corrosion and degradation from bodily fluids. IMD 16 may comprise a hermetic outer housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

During implantation of lead 16 within patient 12, a clinician may attempt to position electrodes 24, 26 of leads 20 such that electrodes 24, 26 are able to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment.

The anatomical region within patient 12 that serves as the target tissue site for stimulation delivered by IMD 14 may be selected based on the patient condition. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MIDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG.

1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more therapy programs. A therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a frequency of the electrical stimulation signal, and, in the case of electrical stimulation pulses, a pulse rate, a pulse width, a waveform shape, and other appropriate parameters such as duration or duty cycle. In addition, if different electrodes are available for delivery of stimulation, a therapy parameter of a therapy program may be further characterized by an electrode combination, which may define electrodes 24, 26 selected for delivery of electrical stimulation and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Examples of bioelectrical brain signals include, but are not limited to, electrical signals generated from local field potentials within one or more regions of brain 28, such as, but not limited to, an electroencephalogram (EEG) signal or an electrocorticogram (ECoG) signal. In some examples, the electrical signals within brain 28 may reflect changes in electrical current produced by the sum of electrical potential differences across brain tissue.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, then the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, and any other information that may be useful for programming into IMD 16. Programmer 14 may also be capable of completing functional tests (e.g., measuring the impedance of electrodes 24, 26 of leads 20).

With the aid of programmer 14 or another computing device, a clinician may select one or more therapy programs for therapy system 10 and, in some examples, store the therapy programs within IMD 16. During a programming session, the clinician may determine one or more therapy programs that may provide efficacious therapy to patient 12 using the devices, systems, and techniques described herein for determining one or more efficacious electrical stimulation parameter settings based on the one or more VTAs expected to result from the delivery of electrical stimulation by IMD 16 according to the respective electrical stimulation parameter setting. Programmer 14 may assist the clinician in the creation/identification of therapy programs by providing physiologically relevant information specific to patient 12.

Example techniques for determining one or more efficacious therapy programs based on the respective VTAs is described in further detail below with respect to FIGS. 4-8. For ease of description, the techniques are primarily described as being employed by programmer 14. In other examples, the techniques may be implemented by any suitable device, such as IMD 16 or another computing device (e.g., a remote computing device such as a cloud computing device), alone or in combination with programmer 14.

In some examples, programmer 14 (or another computing device) is configured to determine one or more therapy programs for IMD 16 that may provide efficacious DBS to patient 12, where the determination is made based on a VTA expected to result from electrical stimulation delivered by IMD 16 via each of the one or more therapy programs. Programmer 14 stores a 3D grid of voxels, which are units of volume. Every point within the space represented by the 3D grid is within one and only one voxel, such that the space is filled by non-overlapping voxels. Each voxel of the 3D grid, or at least some of the voxels of the 3D grid, is assigned a value. Programmer 14 may determine VTAs for one or more therapy programs, register the VTAs to the 3D grid, and determine scores for the one or more therapy programs based on the respective VTAs and the values assigned to voxels of the 3D grid with which the respective VTA overlaps.

The 3D grid may represent a volume of tissue of patient 12, e.g., brain 28 of patient 12. Programmer 14 may register a VTA to the 3D grid using any suitable technique, such as by at least spatially transforming the VTA and 3D grid into a common coordinate system, e.g., thereby aligning the VTA with the volume of tissue represented by the 3D grid. For example, if the 3D grid represents the brain of patient 12, programmer 14 may rotate, scale, and translate the 3D grid, the VTA, or both, as needed, in order to substantially spatially align the expected position of the VTA within brain 28 of patient 12 with the portion of the 3D grid corresponding to such a position. As a result, once registered, the relative position of the VTA and the 3D grid represents the expected position of the VTA within brain 28 of patient 12.

In some examples, as described in further detail below with respect to FIGS. 3 and 8, programmer 14 is configured to generate a graphical user interface (GUI) that presents information regarding the therapy programs and respective scores. In addition to, or instead of being configured to generate the GUI, programmer 14 can be configured to automatically select one or more of the therapy programs for programming IMD 16 based on the respective scores of the therapy programs. Programmer 14 can, for example, automatically transmit a signal to IMD 16 or program IMD 16 with the selected therapy parameter settings, e.g., for chronic (e.g., long-term) therapy delivery or for additional testing on patient 12.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or BLUETOOTH® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system for which therapeutic electrical stimulation parameters may be determined. The techniques described herein can be used to evaluate therapy programs for other therapy systems, such as therapy systems with other configurations of leads and electrodes, therapy systems with more than one IMD, and therapy systems including one or more leadless electrical stimulators (e.g., microstimulators having a smaller form factor than IMD 16 and which may not be coupled to any separate leads). The leadless electrical stimulators can be configured to generate and deliver electrical stimulation therapy to patient 12 via one or more electrodes on an outer housing of the electrical stimulator.

Figure 2:
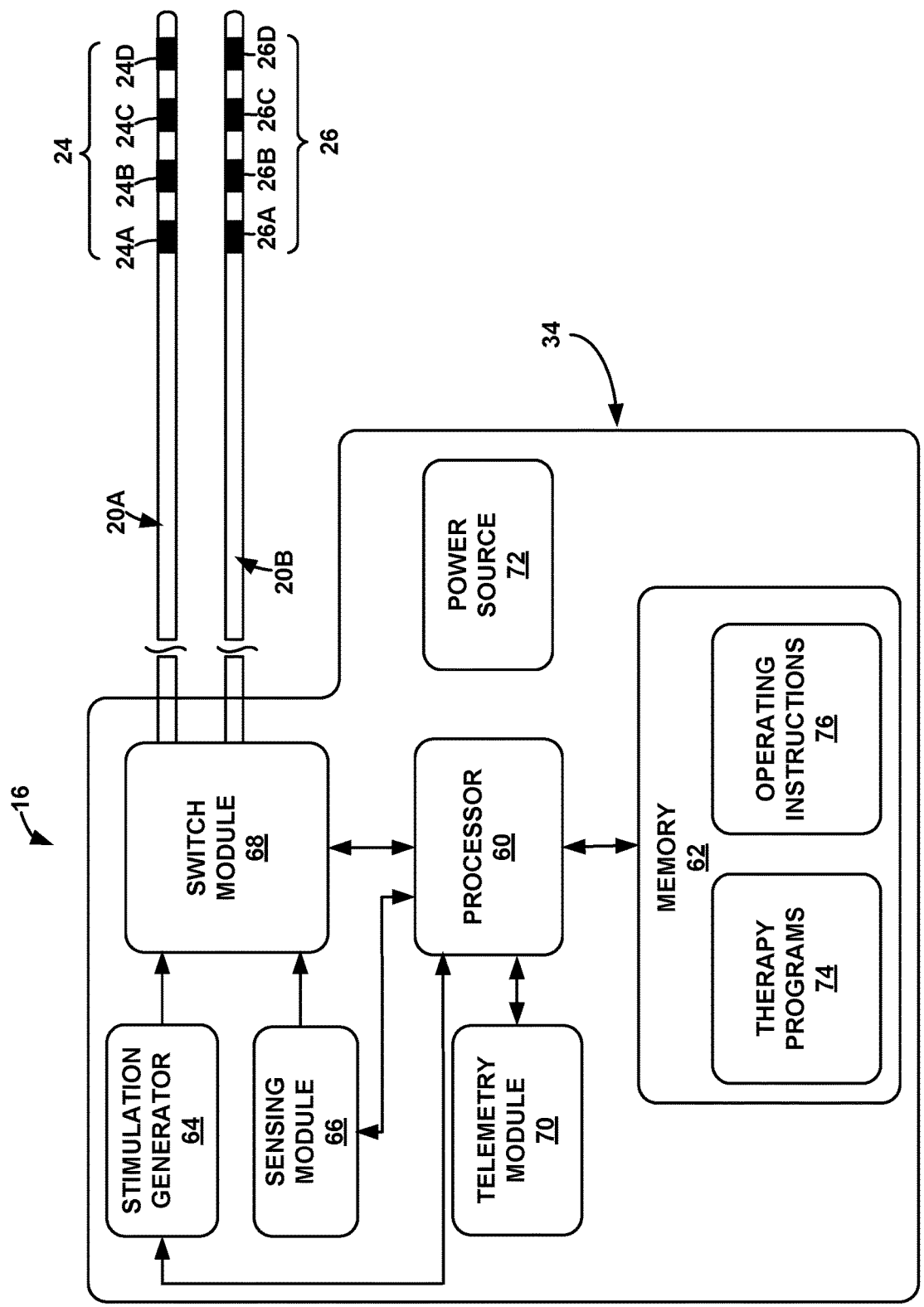
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 76, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. The stimulation signals delivered by IMD 16 may be of any form, such as stimulation pulses, continuous-wave signals (e.g., sine waves), or the like. Operating instructions 76 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more therapy programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68. For example, IMD 16 may include multiple sources of stimulation energy (e.g., current sources).

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on outer housing 34 of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
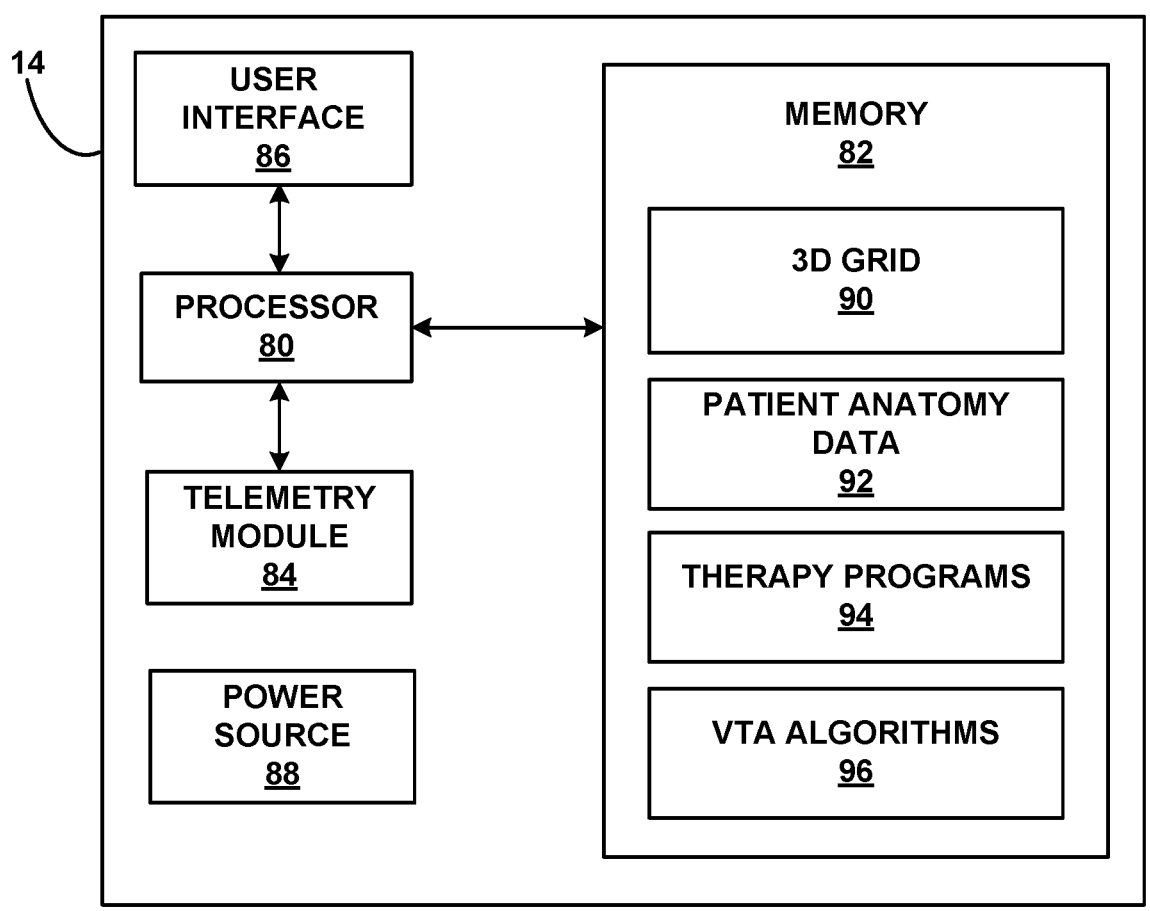
FIG. 3 is a functional block diagram illustrating components of an example medical device programmer.

FIG. 3 is a functional block diagram illustrating components of an example medical device programmer 14. Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80 and programmer 14.

A user, such as a clinician or patient 12, may interact with programmer 14 through user interface 86. User interface 86 includes a display (not shown), such as a LCD or LED display or other type of screen, with which processor 80 may present information related to the therapy (e.g., therapy programs, associated VTAs, one or more 3D grids and voxel values, or any combination thereof). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate though user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores 3D grid 90, anatomy data 92, therapy programs 94, and VTA algorithms 96.

3D grid 90 includes at least one 3D grid of voxels, each voxel having a respective value. Example techniques for determining the values of the voxels of 3D grid 90 are described with respect to FIGS. 4 and 5. 3D grid 90 represents a 3D region of tissue of patient 12. For example, 3D grid 90 may be a 3D representation of the entire brain 28 or a part of brain 28 of patient 12, such that each voxel of 3D grid 90 represents a volume of tissue of brain 28. In another example, 3D grid 90 may be a 3D representation of the brainstem or spinal cord of patient 12, such that each voxel of 3D grid 90 represents a volume of tissue of the central nervous system of patient 12 in tissues other than the brain. In some examples, memory 82 stores a plurality of different 3D grids, such as a grid for each of a plurality of different regions of tissue of patient 12. One 3D grid 90 is described herein in some examples, but in other examples, 3D grid 90 may store any suitable number of 3D grids for different tissue sites of patient 12 or for different patients.

In some examples, 3D grid 90 may be generated based on the anatomy of patient 12. For example, processor 80 may generate 3D grid 90 based on a medical image of patient 12, which indicates the configuration (e.g., the size and shape) of brain 28. In other examples, processor 80 may generate 3D grid 90 based on general patient anatomy data that is not specific to patient 12. In either example, rather than generating 3D grid 90, processor 80 may receive 3D grid 90 from another device.

Processor 80 is configured to generate a VTA for a particular therapy program using VTA algorithms 96 and anatomy data 92 stored by memory 82 to generate the VTA. As noted above, the VTA represents the volume of tissue of patient 12 expected to be activated by the delivery, by a particular electrode combination (e.g., a single electrode in a unipolar configuration or multiple electrodes in a bipolar or multipolar configuration), of electrical stimulation to tissue of patient 12 according to the therapy program. Anatomy data 92 may, for example, include the location of implanted electrodes 24, 26 in brain 28, the anatomical structure of patient 12, and the characteristics of the tissue, such as the impedance or other tissue conductance parameters, proximate to implanted electrodes 24, 26. Anatomy data 92 may be created from any type of imaging modality, such as, but not limited to, computed tomography (CT), magnetic resonance imaging (MM), x-ray, fluoroscopy, and the like. Anatomy data 92 can be patient-specific in some examples, and may be general to more than one patient in other examples.

VTA algorithms 96 may include one or more algorithms with which processor 80 may generate a VTA for a particular set of electrical stimulation parameter values and one or more active electrodes. When IMD 16 delivers electrical stimulation to tissue of patient 12 via an electrode (or combination of electrodes), an electrical field propagates away from the electrode. Processor 80 can reference the algorithms 96 to estimate which neurons will be activated by the electrical field propagating away from an electrode 24, 26 during the delivery of electrical stimulation by the electrode.

In some examples, VTA algorithms 96 may include, for example, electrical field model equations that define how an electrical field propagates away from an origin location. In addition, VTA algorithms 96 may also include a set of equations, a lookup table, or another type of model that defines threshold action potentials of particular neurons that make up the anatomical structure, as defined by anatomy data 92, affected by an electrical field. If the voltage or current amplitude of the electrical field is above the threshold action potential of any neuron within the electrical field, that neuron will be activated, e.g., cause a nerve impulse. Due to changes in electrical current propagation and threshold action potentials (e.g., a threshold voltage) required to activate a neuron, the activation of neurons may vary with the location of tissue around a lead. Some neurons may activate further from the lead with smaller voltages while other neurons may only be activated close to the lead because of a high voltage threshold.

In some examples, memory 82 also stores information regarding the hardware characteristics of leads 20 and processor 80 may generate the VTA based on the hardware characteristics. The hardware characteristics may include, for example, the number or types of leads 20 implanted within patient 12, the number of electrodes 24, 26, the size of each of the electrodes 24, 26, the type of electrodes 24, 26 (e.g., ring electrodes, partial-ring electrodes, segmented electrodes), and the like.

In some examples, processor 80 is configured to generate values for the voxels of 3D grid based on one or more frequency domain characteristics of respective bioelectrical brain signals of patient 12 sensed by IMD 16 or another device during delivery of electrical stimulation by IMD 16 to patient 12 according to one or more test therapy programs. The group of one or more test therapy programs represent therapy parameter values and stimulation electrode combinations that may be delivered to patient 12 in order to determine the effects of a range of electrical stimulation parameters values on brain 28 of patient 12. In some examples, the group of test therapy programs can include therapy programs with a range of stimulation amplitude values and a range of electrode combinations. For example, as described with respect to FIG. 5, the group of test therapy programs include a first set of test therapy programs with a first electrode combination, but different electrical stimulation amplitude values (e.g., covering a preselected range of amplitude values), a second set of test therapy programs with a second electrode combination, but different electrical stimulation amplitude values (e.g., covering the same preselected range of amplitude values as the first set of therapy programs), and so forth for any suitable electrode combinations. In some cases, the electrode combinations are each a single electrode (used to deliver electrical stimulation in unipolar configuration), which may be used in conjunction with a housing electrode of IMD 16, the electrode combinations of each set being a respective electrode 24, 26 of system 10 (such that there are a total of eight electrode combinations and eight sets of test therapy programs).

In some examples, processor 80 may determine the VTAs expected to result from delivery of electrical stimulation according to each test therapy program of a plurality of test therapy programs, register the VTAs to 3D grid 90, and for each test therapy program, determine frequency domain characteristic of a bioelectrical brain signal of patient 12 sensed during delivery of electrical stimulation to patient 12 by IMD 16 according to the test therapy program. Processor 80 may associate and store in memory 82, the frequency domain characteristic for each test therapy program with the VTAs generated based on the respective test therapy program. Processor 80 may then assign at least some voxels of 3D grid 90 a value based on the frequency domain characteristics associated with the VTAs with which the voxels overlap. For example, as described with respect to FIG. 5, processor 80 may assign, to a voxel of 3D grid 90 overlapping with the VTA, a value based on a comparison between each frequency domain characteristic and a value previously assigned to the voxel.

In some examples, instead of determining the values assigned to each voxel of 3D grid, processor 60 may receive the values from another device.

Processor 80 is configured to, after 3D grid 90 is populated with voxel values, either by processor 80 or another device, determine scores for one or more therapy programs evaluated based on the stored 3D grid 90 and values assigned to the voxels of 3D grid 90. In some examples, the therapy programs being evaluated may be different than the test therapy programs. In other examples, at least one of the therapy programs being evaluated is a test therapy program. In some examples, processor 80 may determine the VTAs for one or more therapy programs, and, for each therapy program, determine a score associated with the setting based on the values assigned to voxels of 3D grid 90 with which the respective VTA overlaps. Because the score may be indicative of the therapeutic efficacy of the particular therapy program, the scores may be used to compare the therapeutic efficacy two or more therapy programs. In this way, processor 80, alone or with the aid of a clinician, may determine one or more one or more therapy programs that may provide efficacious electrical stimulation therapy for patient 12 based on the scores.

Processor 80 may store the therapy programs and associated scores in memory 82 as stored therapy programs 94. A clinician may review the stored therapy programs 94 and associated scores, e.g., during programming of IMD 16, to select one or more therapy programs with which IMD 16 may deliver efficacious electrical stimulation to patient 12. For example, the clinician may interact with user interface 86 to retrieve the stored therapy programs 94 and respective scores.

In some examples, processor 80 is configured to generate and present, via a display of user interface 86, a graphical user interface (GUI) that presents a list of therapy programs and the respective scores. A user (e.g., a clinician) may interact with the GUI to manipulate the list of therapy programs. For example, in response to receiving user input requesting the list of therapy programs be ordered by score, processor 80 may reorganize the list of therapy programs based on the respective scores (e.g., from highest to lowest scores or vice versa). In some examples, a user may also interact with the graphical user interface to select a particular therapy program, and, in response to receiving the user input, programmer 14 may provide additional details about the therapy program, such as a graphical representation of the VTA expected to result from the delivery of electrical stimulation according to the therapy program, information about the bioelectrical brain signal sensed within brain 28 during therapy delivery according to the therapy program, or any combination thereof. As another example, the additional details presented by programmer 14 may include details about the individual parameter settings of the therapy program, such as the electrical stimulation parameter values, electrode combination, or both.

In addition, in some examples, processor 80 may be configured to generate a GUI, via user interface 86, that visually illustrates, for a particular therapy program, how the VTA expected to result from delivery of electrical stimulation therapy according to the therapy program overlaps with 3D grid 90. 3D grid 90 may, in some examples, be presented in the GUI to resemble the region of tissue represented by 3D grid 90. For example, 3D grid 90 may be presented in the GUI to have visual characteristics that resemble a human brain. In other examples, 3D grid 90 may be presented in the GUI in a more conceptual manner, such as a 3D line diagram that is not in the shape of the associated anatomical region of patient 12 represented by 3D grid 90. In either examples, the borders between adjacent voxels of 3D grid 90 may be displayed or may be removed from the GUI, e.g., in response to user input. A user may view the GUI to visualize how the therapy program may affect tissue of patient 12.

In addition, in some examples, regardless of how 3D grid 90 is presented, processor 14 may display the values of each of the voxels at the portion of 3D grid 90 corresponding to the voxel location. In this way, the user may visualize the regions of tissue that may be associated with relatively efficacious therapy (e.g., associated with relatively high values, or, in some examples, relatively low values, depending on the scale), and the regions of tissue that may be associated with less efficacious therapy.

In some examples, patient 12, a clinician or another user may interact with user interface 86 of programmer 14 in other ways to manually select therapy programs from the stored therapy programs 94 for programming IMD 16, generate new therapy programs, modify stored therapy programs 94, transmit the selected, modified, or new therapy programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. In other examples, traditional batteries (e.g., nickel cadmium or lithium ion batteries) may be used. In addition, programmer 14 may be directly coupled to an alternating current outlet to operate.

Figure 4:
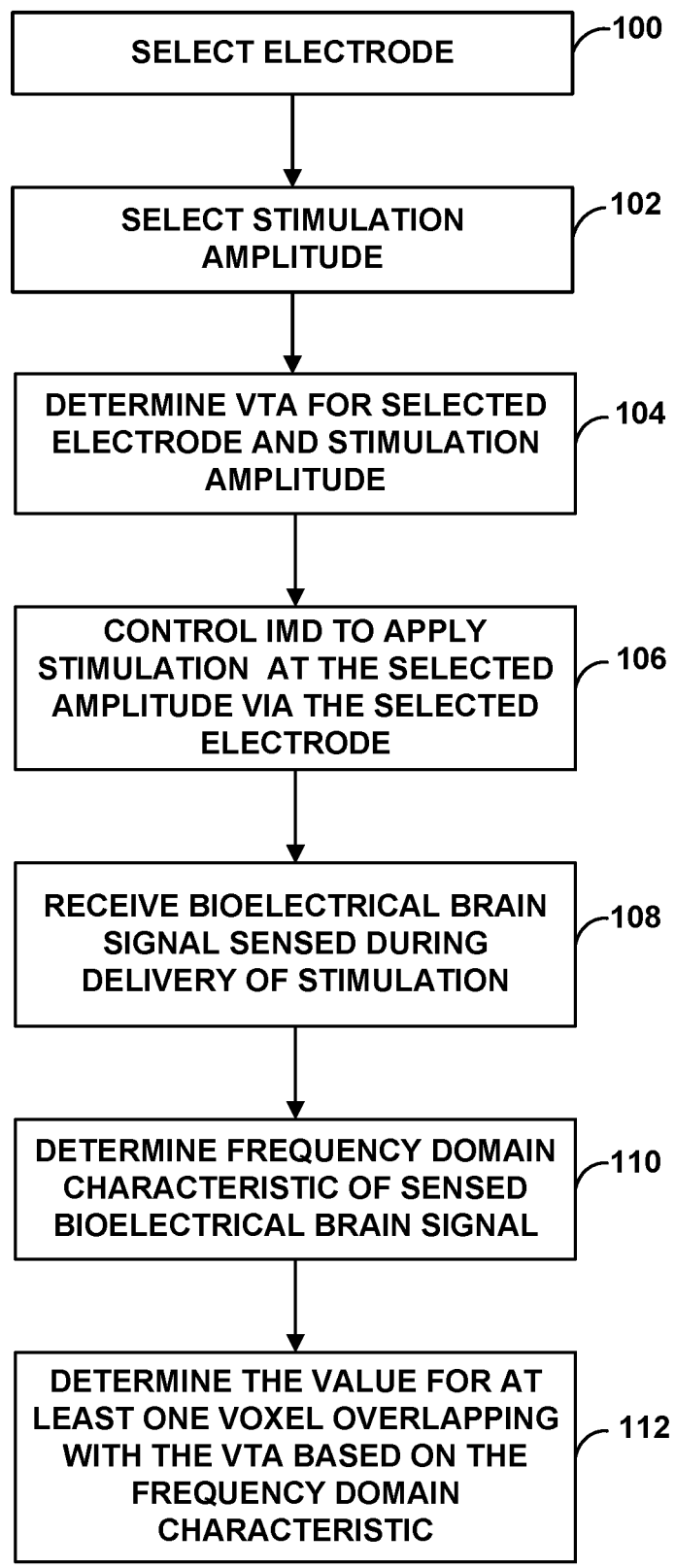
FIG. 4 is a flow diagram illustrating an example technique for determining the values assigned to voxels of a 3D grid.

FIG. 4 is a flow diagram illustrating an example technique for determining the values assigned to the voxels of 3D grid 90. In the example shown in FIG. 4, each voxel is assigned only one value. In other examples, each voxel may be assigned multiple values, with each value for each voxel corresponding to a different frequency domain characteristic of a sensed bioelectrical brain signal. In a further example, each voxel may be assigned one value based on the power in the beta band sensed during delivery of stimulation, a second value based on the power in the theta band sensed during delivery of stimulation, and a third value based on the power in the gamma band sensed during delivery of stimulation. While the techniques shown in FIGS. 4-7, 9-11, and 13 are primarily described as being performed by processor 80 of programmer 14, in other examples, a processor of another device, such as processor 60 of IMD 16, can perform any part of the techniques shown in FIGS. 4-7, 9-11, and 13, alone or in combination with processor 80.

In order to determine the values assigned to the voxels of 3D grid 90, processor 80 may determine the VTA for one or more test therapy programs, and determine frequency domain characteristics of bioelectrical signals indicative of the response of patient 12 to the delivery of electrical stimulation according to the one or more test therapy programs. Processor 80 may then determine the values of at least some voxels of 3D grid 90 based on the frequency domain characteristics. In the example shown in FIG. 4, the one or more test therapy programs differ from each other based on the electrode that is selected to deliver the electrical stimulation therapy to patient 12 in a unipolar stimulation configuration, the stimulation amplitude, or both. In a unipolar configuration, the active electrode with which electrical stimulation signals are delivered is referenced to an electrode carried by IMD housing 34 or "can." Thus, processor 80 may determine the one or more test therapy programs by modifying at least one of the stimulation electrode, the stimulation amplitude, or both. In other examples, however, processor 80 may determine the one or more test therapy programs using another technique, such as by selecting one or more predetermined test therapy programs from memory 82. The stored test therapy programs 94 may be, for example, selected by a clinician and stored by memory 82 of programmer 14 or a memory of another device, such as IMD 16 or a remote database.

In accordance with the technique shown in FIG. 4, processor 80 selects an electrode (100) from a plurality of electrodes 24, 26 and selects an electrical stimulation amplitude value (also referred to herein as "stimulation amplitude value" or an "amplitude value") (102). In some examples, memory 82 of programmer 14 stores a predetermined maximum amplitude value (or other stimulation parameter value), and processor 80 selects an initial amplitude value (102) to be less than the predetermined maximum. In some examples, the predetermined maximum amplitude value is 10.0 volts; other predetermined maximum amplitude values may be applied in other examples. In some examples, a clinician may select the predetermined maximum value to be the amplitude value (or other stimulation parameter value or combination of values) at which the stimulation intensity is at a maximum desired intensity for patient 12 or a group of patients. As another example, a clinician may select the predetermined maximum value to be the amplitude value to be the maximum amplitude value permitted by the hardware, software, or both, of IMD 16.

The initial amplitude value may be a part of an initial set of electrical stimulation parameter values that processor 80 selects in order to start the determination of voxel values. In some examples, the initial set of electrical stimulation parameter values may include values for a pulse width, a frequency, and an amplitude of electrical stimulation. The pulse width and frequency may remain fixed at the values of the initial set of electrical stimulation parameter values, while processor 80 may adjust the amplitude from the initial amplitude value in order to determine the voxel values. In some examples, the pulse width is about 60 milliseconds (ms) and the frequency is about 135 Hertz (Hz).

Processor 80 determines the VTA based on the selected amplitude value (104), where the VTA indicates the volume of tissue that is expected (e.g., estimated) to be activated by the stimulation field resulting from delivery of electrical stimulation by IMD 16 via the selected electrode (in a unipolar configuration), the electrical stimulation being generated by IMD 16 in accordance with the selected stimulation amplitude value and the other stimulation parameter values of the initial set. Processor 80 can determine the VTA using any suitable technique, such as the example technique described with respect to FIG. 9. As described with respect to FIG. 9, in some examples, processor 80 utilizes an algorithm (e.g., stored as a VTA algorithm 96 in memory 82 of programmer 14) to determine an electrical field that indicates the stimulation field that will propagate away from the electrode when an initial set of stimulation parameter values is used to deliver electrical stimulation via the electrode. Based on the electrical field and anatomy data 92 (e.g., one or more impedance characteristics of patient neural tissue proximate to the selected electrode), which in some cases may be patient-specific, processor 80 may estimate the volume of tissue of brain 28 (or other tissue areas) that will be activated by the electrical field.

Example techniques that processor 80 may use to determine a VTA (104) are described in commonly-assigned U.S. Pat. No. 7,822,483 to Stone et al., entitled, "ELECTRICAL AND ACTIVATION FIELD MODELS FOR CONFIGURING STIMULATION THERAPY" and issued on Oct. 26, 2010, and commonly-assigned U.S. Patent Application Publication No. 2013/0289380 by Molnar et al., entitled, "VISUALIZING TISSUE ACTIVATED BY ELECTRICAL STIMULATION," and filed on Mar. 14, 2013. The entire content of U.S. Pat. No. 7,822,483 to Stone et al. and U.S. Patent Application Publication No. 2013/0289380 by Molnar et al. is hereby incorporated by reference.

In accordance with some examples described in U.S. Patent Application Publication No. 2013/0289380 by Molnar et al., a volume of activation of tissue resulting from delivery of electrical stimulation according to a set of stimulation parameter values may be determined based on a uniform or non-uniform grid of neuron representatives that indicate the neurons of the tissue of the patient proximate electrodes 24, 26. Each neuron representative may be associated with a threshold value of activation (also referred to herein as an "activation threshold value" or "activation threshold"). The threshold value for each neuron representative may be obtained using a binary search algorithm. The threshold value is an electrical stimulation voltage or current amplitude, that when applied to an actual neuron of the type being modeled by processor 80, results in a propagating action potential along the neuron. In some examples, the action potential is considered to have excited, or "activated," the neuron representative if the transmembrane potential reached a threshold greater than 0 mV. As used herein, the threshold value of activation may be referred to as a threshold, an activation threshold, or a propagation threshold.

Prior to, after, or simultaneously with the generation of the VTA (104), processor 80 controls IMD 16 to deliver, to patient 12, electrical stimulation at the selected amplitude via the selected electrode (106). For example, processor 80 may transmit a control signal to IMD 16 via the respective telemetry modules 84, 70 that causes processor 60 (FIG. 2) of IMD 16 to control stimulation generator 64 (FIG. 2) to generate and deliver the electrical stimulation. In other examples, a clinician may control IMD 16 to deliver, to patient 12, electrical stimulation at the selected amplitude via the selected electrode. The control signal may also cause processor 60 of IMD 16 to control sensing module 66 of IMD 16 (FIG. 2) to sense a bioelectrical brain signal during the delivery of electrical stimulation at the selected amplitude via the selected electrode. For example, at the same time stimulation generator 64 is delivering electrical stimulation to patient 12, sensing module 66 may sense the bioelectrical brain signal with different electrodes than the electrode used to deliver the electrical stimulation. The electrodes with which IMD 16 senses the bioelectrical brain signal can be, for example, directly adjacent to (e.g, on either side of) the electrode selected for delivering the stimulation.

Processor 80 receives the sensed bioelectrical brain signal from IMD 16 (108) and determines a frequency domain characteristic of the sensed bioelectrical brain signal (110). The frequency domain characteristic of the bioelectrical brain signal (or other sensed biosignal) may include, for example, a mean, median, lowest or highest power level (or energy) within one or more frequency bands of interest of the bioelectrical brain signal, a ratio of the power level in two or more frequency bands, a correlation in change of power between two or more frequency bands, a pattern in the power level of one or more frequency bands over time, and the like. Processor 80, alone or with the aid of a clinician, may select the one or more frequency bands of interest for which the frequency domain characteristic of the bioelectrical brain signal are determined based on the patient condition.

In some examples, the frequency domain characteristic may be based on a relative power level in a particular frequency band or a plurality of frequency bands. While "power levels" within a selected frequency band of a sensed bioelectrical brain signal are generally referred to herein, the power level may be a relative power level. A relative power level may include a ratio of a power level in a selected frequency band of a sensed brain signal to the overall power of the sensed brain signal. The power level in the selected frequency band may be determined using any suitable technique. In some examples, processor 80 may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by IMD 16.

The overall power of a sensed bioelectrical brain signal may be determined using any suitable technique. In one example, processor 80 (or another device, such as IMD 16) may determine an overall power level of a sensed bioelectrical brain signal based on the total power level of a swept spectrum of the brain signal. To generate the swept spectrum, processor 60 of IMD 16 may control sensing module 66 to tune to consecutive frequency bands over time, and processor 60 of IMD 16 or processor 80 of programmer 14 may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

Processor 80 determines the value for at least one voxel of 3D grid 90 overlapping with the VTA based on the frequency domain characteristic (112). Processor 80 may register the VTA with 3D grid 90 in order to determine which voxels of 3D grid 90 overlap with the VTA. Processor 80 may consider a voxel to overlap with the VTA if at least 50 percent (%) of the voxel sits within the VTA. In some examples, processor 80 may assign voxels that only partially sit within the VTA a value that is a percentage of the value of voxels that are 100% within the region, corresponding to the percentage of the volume of the voxels that are within the region times the value for voxels that are 100% within the region.

In some examples, the value assigned to a voxel that is entirely within the VTA may be the frequency domain characteristic. For example, if the frequency band of interest is the beta band (as it may be in the case of Parkinson's disease), the value may be the change in the power level in the beta band relative to a baseline value. In some cases, the greater the reduction in the power level in the beta band of a bioelectrical brain signal sensed during delivery of electrical stimulation, the more effective the electrical stimulation therapy may be. Thus, in some examples, the change in the power level in the beta band relative to the baseline value may be a meaningful metric with which a particular therapy program may be evaluated. Accordingly, in some examples, the value assigned to a voxel is indicative of, e.g., equal to, a change in the power level in the beta band relative to a baseline value.

In other examples, processor 80 may assign the voxel another value determined based on the frequency domain characteristic. For example, memory 82 may store information that associates a plurality of ranges of frequency domain characteristics with respective numerical values, and processor 80 may select the range in which the determined frequency domain characteristic falls and select the associated numerical value as the value assigned to the voxels of the 3D grid 90.

In some cases, processor 80 may determine the VTA for each test therapy program of a plurality of different test therapy programs, and determine the frequency domain characteristics of the bioelectrical brain signals resulting from the delivery of the electrical stimulation according to the respective test therapy programs. The plurality of test therapy programs can differ from each other based on, for example, the stimulation electrode, the stimulation amplitude, or both (e.g., selected during different iterations of blocks 100 and 102 in FIG. 4). Processor 80 may determine the voxel values for 3D grid 90 based on the group of determined frequency domain characteristics (112). For example, if a voxel overlapped with the VTAs resulting from therapy delivery according to a plurality of test therapy programs, then processor 80 may assign the voxel a value that is based on the frequency domain characteristics of the group of bioelectrical brain signals sensed during the delivery of each of the therapy programs. For example, processor 80 may assign the voxel a value that is or is based on the highest frequency domain characteristic of the group (e.g., the greatest change in the beta band power level), the lowest frequency domain characteristic of the group, the average frequency domain characteristic of the group, or the median frequency domain characteristic of the group.

Processor 80 may associate the determined values for the voxels with the voxels and store the information as part of 3D grid 90 in memory 82 of programmer 14.

Figure 5:
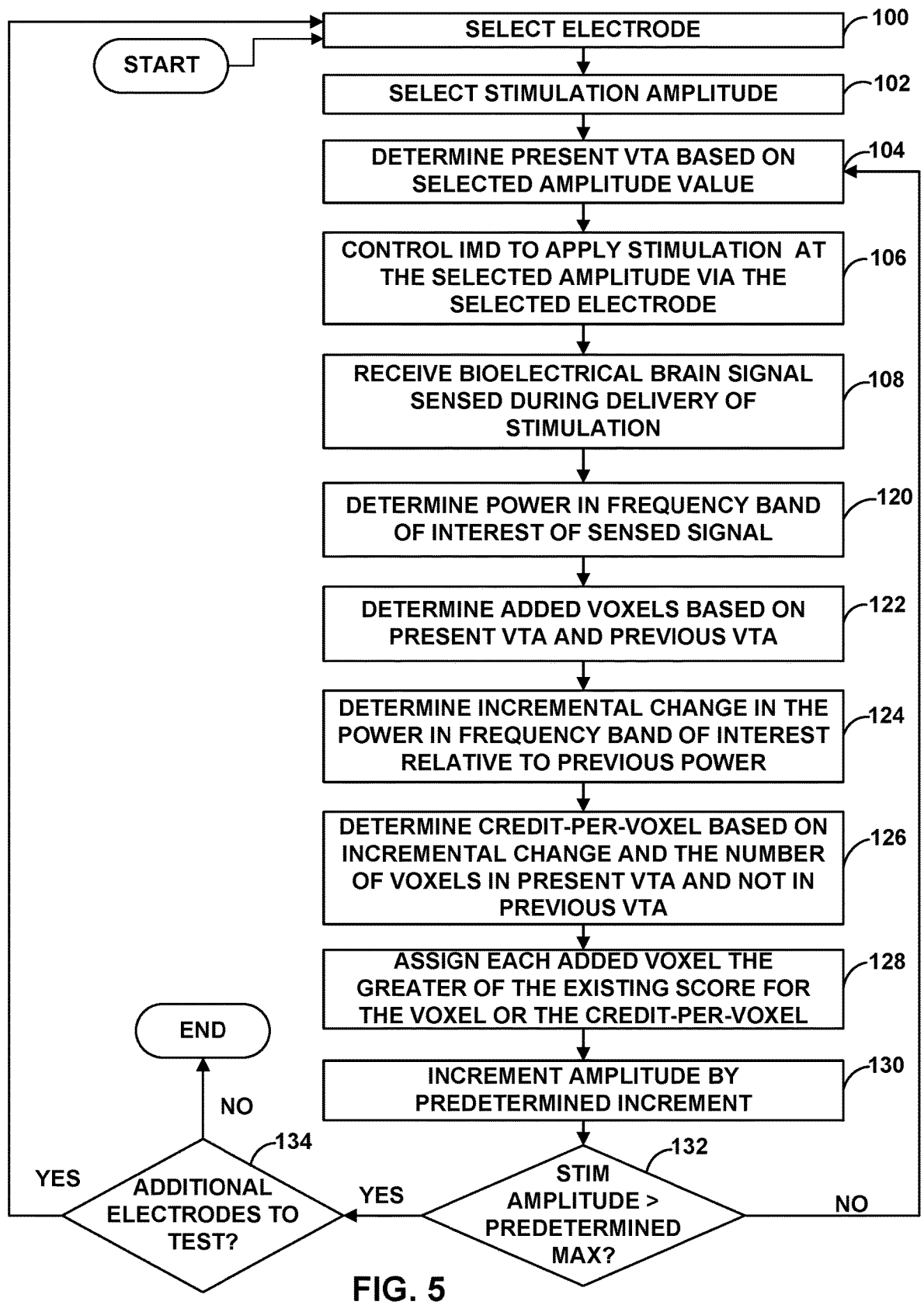
FIG. 5 is a flow diagram illustrating another example technique for determining the values assigned to voxels of a 3D grid.

FIG. 5 illustrates another example technique that processor 80 may implement in order to assign a voxel of 3D grid 90 a value based on the frequency domain characteristics associated with a plurality of different therapy programs. As with the technique shown in FIG. 4, in the technique shown in FIG. 5, processor 80 selects an electrode (100), selects a stimulation amplitude value (102) (e.g., starting with an initial amplitude value), and determines a VTA expected to result from delivery of electrical stimulation with the selected electrode (or selected electrode combination) and selected stimulation amplitude (104). The determined VTA is referred to as a "present VTA" in the description of FIG. 5, in that the determined VTA is the VTA for the presently selected test therapy program (as defined by the selected electrode, selected stimulation amplitude value, and other parameter values of the initial parameter set). In accordance with the technique shown in FIG. 5, processor 80 controls IMD 16 to apply electrical stimulation to patient 12 at the selected amplitude via the selected electrode (106), and receives a bioelectrical brain signal sensed by IMD 16 or another device during delivery and/or after delivery of the electrical stimulation (108).

Processor 80 determines a frequency domain characteristic of the sensed bioelectrical brain signal, which, in the example shown in FIG. 5, is a power level in a frequency band of interest (120). As discussed above with respect to FIG. 4, the frequency band of interest may differ depending on the patient condition for which system 10 is implemented to help manage.

Processor 80 determines the voxels of 3D grid 90 that overlap with the present VTA and determines which voxels, if any, were added relative to the voxels of 3D grid 90 that overlapped with a previously determined VTA (122). The previously determined VTA can be, for example, a VTA determined based on a previously tested therapy program (e.g., a previously selected stimulation amplitude, a previously selected stimulation electrode, or both). Processor 80 may store the previously determined VTA in memory 82. The previously determined VTA may be associated with a power level of a frequency domain characteristic of the bioelectrical brain signal sensed during delivery of the electrical stimulation according to the previously tested therapy program. This power level may be referred to as a "previous power level." If the present VTA is the first-determined VTA and no previously determined VTA is stored by memory 82, then processor 80 may determine the previously determined VTA to be an empty list of voxels and the previous power level to be 0.

Processor 80 determines an incremental change in the power level in the frequency band of interest of the sensed bioelectrical brain signal (sensed during delivery of electrical stimulation according to the presently selected test therapy program) relative to the previous power level (124). In some examples, the incremental change may be the absolute value of the difference between the power level in the frequency band of interest of the sensed bioelectrical brain signal and the power previous power level.

Processor 80 determines a credit-per-voxel based on the incremental change and the number of voxels in the present VTA and not in the previous VTA (126). The number of voxels in the present VTA and not in the previous VTA may be referred to as a "voxel count." In some examples, processor 80 determines the credit-per-voxel by at least determining the incremental change in the power level in the frequency band of interest of the sensed bioelectrical brain signal relative to the previous power level divided by voxel-count. The credit-per-voxel may equal the incremental change in the power level in the frequency band of interest of the sensed bioelectrical brain signal relative to the previous power level divided by voxel-count.

For each voxel in the present VTA and not in the previous VTA, processor 80 assigns the voxel a value that is the greater of the existing score for the voxel, which may be the score assigned to the voxel based on previous test therapy programs, or the credit-per-voxel (128). Processor 80 may then associate each added voxel the assigned value in memory 82, as part of the stored 3D grid 90 information.

After assigning each voxel in the present VTA and not in the previous VTA a value, processor 80 may store the present VTA as a previous VTA and the power level in the frequency band of interest as a previous power level.

In addition, processor 80 may increase the stimulation amplitude by a predetermined increment (130). The predetermined increment may be selected using any suitable criteria. In some examples, the size of the increment by which the stimulation amplitude (or other parameter) is adjusted may be selected to be large enough to result in a change to the VTA, but small enough to provide a gradual change in size to the VTA. For example, the size of the increment by which processor 80 may adjust the stimulation amplitude may be 0.5 volts, although other increments can be used in other examples.

Processor 80 determines whether the stimulation amplitude is greater than a predetermined maximum (132), which, as discussed with respect to FIG. 4, may be stored by memory 82. In response to determining the stimulation amplitude is not greater than the predetermined maximum ("NO" branch of block 132), processor 80 determines an updated present VTA based on the increased stimulation amplitude value and the previously selected stimulation electrode (104), and repeats the technique shown in FIG. 5 to determine the credit-per-voxel based on the present VTA and the power level in the frequency band of interest of a bioelectrical brain signal sensed during the delivery of electrical stimulation with the increased stimulation amplitude value (126) and to determine the value assigned to each voxel in the present VTA and not in the previous VTA (128).

In the example shown in FIG. 5, processor 80 determines the VTAs and voxel values for at least two electrodes 24, 26 of leads 10, such as for each electrode 24, 26. Thus, processor 80 may select an electrode and update the voxel values of 3D grid 90 based on the VTAs resulting from each stimulation amplitude setting starting with an initial stimulation amplitude setting and until the predetermined maximum is reached ("YES" branch of block 132). Processor 80 may determine if there are additional electrodes (or electrode combinations) to test using any suitable technique. In some examples, processor 80 stores a list of electrodes 24, 26 to test, and moves through the list in a predetermined order. Thus, if processor 80 reaches the end of the list, processor 80 may determine there are no additional electrodes to test. In response to determining the stimulation amplitude is greater than the predetermined maximum, processor 80 determines whether there are additional electrodes to test (134). In response to determining there are no additional electrodes to test ("NO" branch of block 134), processor 80 may end the technique shown in FIG. 5.

In response to determining there are additional electrodes to test ("YES" branch of block 134), e.g., if there is another electrode in the list, processor 80 may select another electrode and repeat the technique shown in FIG. 5 to update the voxel values of 3D grid 90 based on the VTAs resulting from each stimulation amplitude setting until the predetermined maximum amplitude is reached.

After values are assigned to at least some voxels of 3D grid 90, e.g., using the technique of at least one of FIG. 4 or FIG. 5, processor 80 may use 3D grid 90 to select one or more therapy programs that may provide efficacious therapy to patient 12. For example, processor 80 may determine scores for a plurality of different therapy programs based on the values of the voxels of 3D grid 90 with which the respective VTAs overlaps, and select one of the therapy programs for therapy delivery by IMD 16 based on a comparison of the scores.

Figure 6:
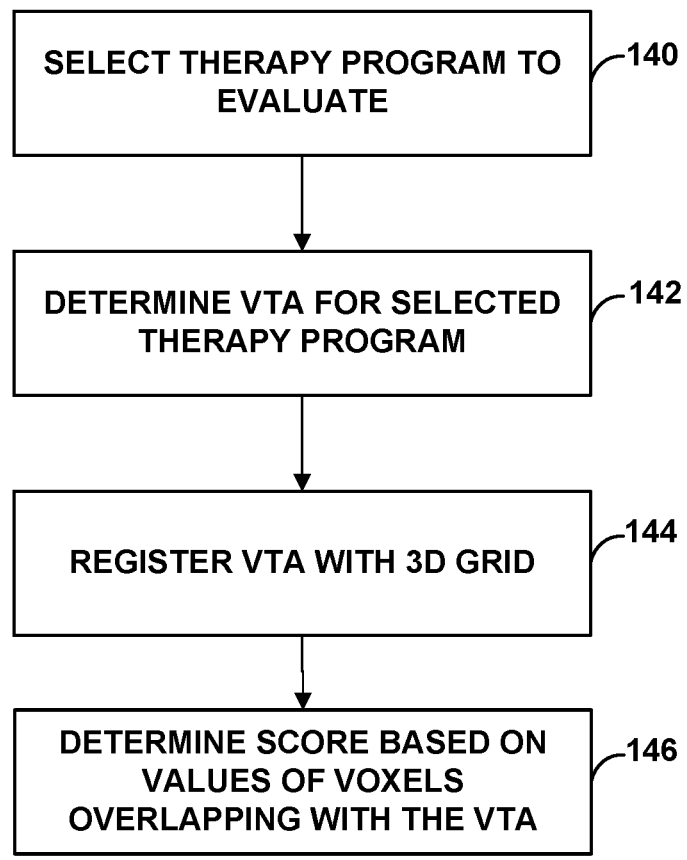
FIG. 6 is a flow diagram illustrating an example technique for determining a score for a therapy program based on a volume of tissue expected to be activated by delivery of electrical stimulation therapy according to the therapy program.

FIG. 6 is a flow diagram of an example technique for scoring one or more therapy programs based on 3D grid 90. Processor 80 selects a therapy program to evaluate (140). Processor 80 may select the therapy program using any suitable technique. In some examples, a clinician inputs, via user interface 86 of programmer 14 (FIG. 3), one or more therapy programs to evaluate. Processor 80 may store the one or more inputted therapy programs in memory 82 and select the therapy program (140) from the stored therapy programs 94 (FIG. 3). In other examples, a clinician may input an electrical stimulation parameter setting, such as a particular stimulation amplitude value or an electrode combination, and processor 80 may select the therapy program by combining the inputted electrical stimulation parameter setting with other electrical stimulation parameter values, such as the electrical stimulation parameter values of the initial stimulation parameter set discussed above. In other examples, memory 82 of programmer 14 may store a standard set of therapy programs to evaluate.

Processor 80 determines the VTA for the selected therapy program (142), e.g., using any of the techniques described above with respect to FIGS. 4 and 5 (block 104). After processor 80 determines the VTA, processor 80 registers the VTA with 3D grid 90 (144). For example, processor 80 may align the VTA with the coordinate system used by 3D grid 90 in order to align the VTA with the particular volume of tissue of patient 12 represented by 3D grid 90.

After registering the VTA with 3D grid 90, processor 80 determines the voxels with which the VTA overlaps and determines the score for the therapy program based on the voxel values (146). In some examples, processor 80 may consider a voxel to overlap with the VTA if at least 50% of the voxel sits within the VTA. In some examples, processor 80 may determine the score using only a percentage of the value assigned to any voxel that is not 100% within the VTA. For instance, the score may take into account only a percentage of the value assigned to a voxel based on the percentage of the volume of the voxel that is within the region.

In some examples, the score for the therapy program is the sum of the values of the voxels with which the VTA overlaps. In other examples, the score for the therapy program is a mathematical function of the respective sums of the various values for the voxels with which the VTA overlaps, such as a weighted combination of the sum of the voxels' values associated with power in the beta frequency band, the sum of the voxels' values associated with power in the theta frequency band, and the sum of the voxels' values associated with power in the gamma frequency band. The weights used in the mathematical function may be pre-programmed by a clinician, or they may be based on past evidence regarding the relationship between therapy program scores and patient outcomes.

Figure 7:
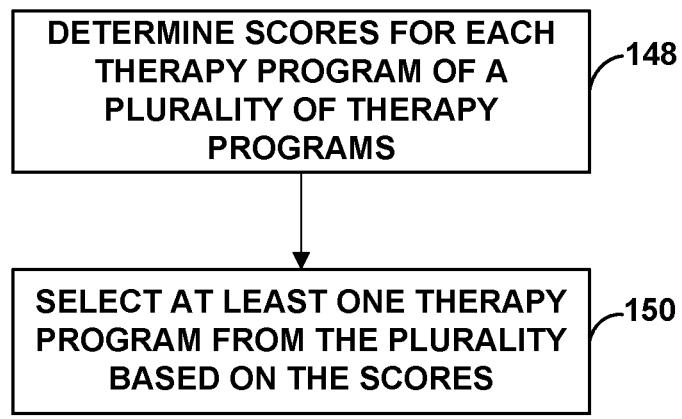
FIG. 7 is a flow diagram of an example technique for selecting a therapy program based on the score associated with the therapy program.

FIG. 7 is a flow diagram of an example technique for selecting a therapy program based on the score associated with the therapy program. Processor 80 may determine the scores for each therapy program of a plurality of therapy programs (148), e.g., using the technique described with respect to FIG. 6. Processor 80 may then select at least one therapy program from the plurality of therapy programs based on the scores (150). For example, processor 80 may select the therapy program having the highest score, or the two or more therapy programs having the highest score and program IMD 16 with the selected therapy programs. If programmer 14 automatically programs IMD 16 with the selected therapy programs, then IMD 16 may then store the therapy programs and processor 60 of IMD 16 may control therapy delivery to patient 12 with the stored therapy programs.

In other examples, rather than automatically selecting the therapy programs based on the scores, processor 80 may present, via a display of user interface 86, the therapy programs having the relatively highest scores or all of the therapy programs and the respective scores, and a user may then use the list of therapy programs and respective scores as guidance for programming DBS therapy for patient 12. Processor 80 may, for example, receive user input, via user interface 86 (FIG. 3), selecting one or more therapy programs from a plurality of therapy programs. Processor 80 may then program IMD 16 with the selected one or more therapy programs.

For example, processor 80 may be configured to generate and present, via a display of user interface 86, a list of therapy programs and respective scores. FIG. 8 is a conceptual illustration of a medical device programmer 14, which includes display 152 presenting a GUI 154 that includes a list of therapy programs. Display 154 may be a LCD, touch screen display, or another type of monochrome or color display capable of presenting information to a user, e.g., a clinician. The therapy programs are designated Program A, Program B, and so forth and, along with associated scores. In the example shown in FIG. 8, the scores are displayed as unitless numbers ranging from negative 10,000 to positive 30,000. In other examples, the scores may be displayed as calculated percentages with the therapy program associated with the highest relative efficacy receiving a calculated percentage of 100% and successively lower ranked therapy programs receiving lesser calculated percentages based on the ratio between their score and the score of the top rated therapy program. Scores 154 are objective values (e.g., unrelated to subjective patient feedback regarding perceived therapeutic efficacy) that may indicate the relative efficacy of the associated therapy program. Because scores 154 are based on physiologic data specific to patient 12, scores 154 may be a useful metric for comparing therapy programs and their relative efficacy for the particular patient 12

A user (e.g., a clinician) may quickly ascertain, based on the information displayed by GUI 154, the therapy programs having the relatively highest scores. In this way, GUI 154 may guide the selection of one or more therapy programs that may provide efficacious therapy to patient 12. In some examples, a user may interact with programmer 14 to order the list of therapy programs based on the scores. For example, the user may interact with one or more buttons 160 to provide input to processor 80 requesting the list be ordered in a particular manner and, in response to receiving the input, processor 80 may reorder the list according to the inputted order. In some cases, the clinician may wish to maximize the score and may determine which therapy program resulted in the relatively highest score by ordering the list of therapy programs in descending order, with the therapy program associated with the highest score being listed first in the displayed list. Ordering the list of therapy programs according to user-chosen criteria may further enable the clinician to quickly identify the therapy programs that may be efficacious.

In some examples, the therapy programs being evaluated may differ from each other based on only one stimulation parameter setting, such as the electrode combination or the stimulation amplitude. Thus, the scores may represent the efficacy of different settings of an individual stimulation parameter. In some examples, instead of, or in addition to, displaying the therapy programs, GUI 154 may display the specific stimulation parameter setting that differs between the therapy programs. In this way, a user may reference GUI 154 to quickly compare different stimulation parameter settings using the determined scores. For example, if Programs A-H shown in FIG. 8 have different electrode combinations (e.g., different electrodes) and the other stimulation parameter values are the same between Programs A-H, then processor 80 may generate GUI 154 to present an indication of the electrode combinations (e.g., specific electrodes in the case of unipolar electrical stimulation) associated with the scores.

The foregoing contemplates determining scores based, at least in part, on characteristics of sensed biological signals. In some cases, it may be desirable to adjust these scores based on side effects. For instance, if a particular therapy program results in one or more side effects experienced by the patient, the score that was originally assigned to the program based on the sensed biological signal may be adjusted downward. Example side effects may include incontinence, tingling, loss of balance, paralysis, slurred speech, loss of memory, loss of inhibition, or other neurological problems. As an example, if delivery of therapy according to a particular therapy program results in the patient experiencing slurred speech, the score associated with that program may be adjusted downward by a predetermined amount because of the manifestation of the slurred speech. That predetermined amount may be a predetermined fixed value, a predetermined percentage of the original assigned score, or by some other determined value.

The amount by which the original score is adjusted downward may be determined based on the particular side effect or a particular combination of side effects experienced by the patient. For example, the amount by which a score is adjusted downward may be different for slurred speech than it is for loss of memory, and so on. In some cases, the amount by which the originally-assigned score is adjusted downward may be patient-specific. That is, the patient and/or clinician may be allowed to determine the undesirability of a particular side effect for that patient and assign the value to be used in the downward adjustment of a score if that side effect manifests itself when therapy is delivered according to that program. For instance, the patient may determine which side effects are found to be particularly debilitating and assign larger adjustment values to those side effects. In other examples, the adjustment values may be determined, at least in part, based on patient population data. For instance, from patient population data, it may be determined that a certain side effect is particularly debilitating for patients exhibiting a particular disease state and thus for those patients, the manifestation of that side effect should result in a larger downward adjustment value.

In some examples, the determination as to whether the delivered therapy is resulting in side effects may occur over time. For instance, the clinician may initially program a patient's medical device to deliver therapy according to one or more programs associated with the highest scores derived from the sensed biological signals. After this initial programming of the device, the patient may go about daily life. During this time, the patient may determine whether any of the one or more programs that are providing therapy result in side effects. The patient may provide information on any experienced side effects and the program causing such side effects to the clinician either prior to, or during, a next programming session. This information may be provided to allow the clinician to determine revised scores for the programs for use in re-programming the therapy during the next programming session. For instance, the clinician may downwardly adjust the scores for any programs associated with side effects so that new ranking of program efficacy is obtained for the next programming session. In some cases, rather than merely adjust scores downward for programs resulting in side effects, those programs may instead be removed entirely from a list of available programs to be used in programming a patient's medical device. In some instances, this re-ranking of program efficacy may be completed even before the patient arrives at the clinic for the next programming session, thereby improving efficiency of the visit for both the patient and clinician.

Figure 8:
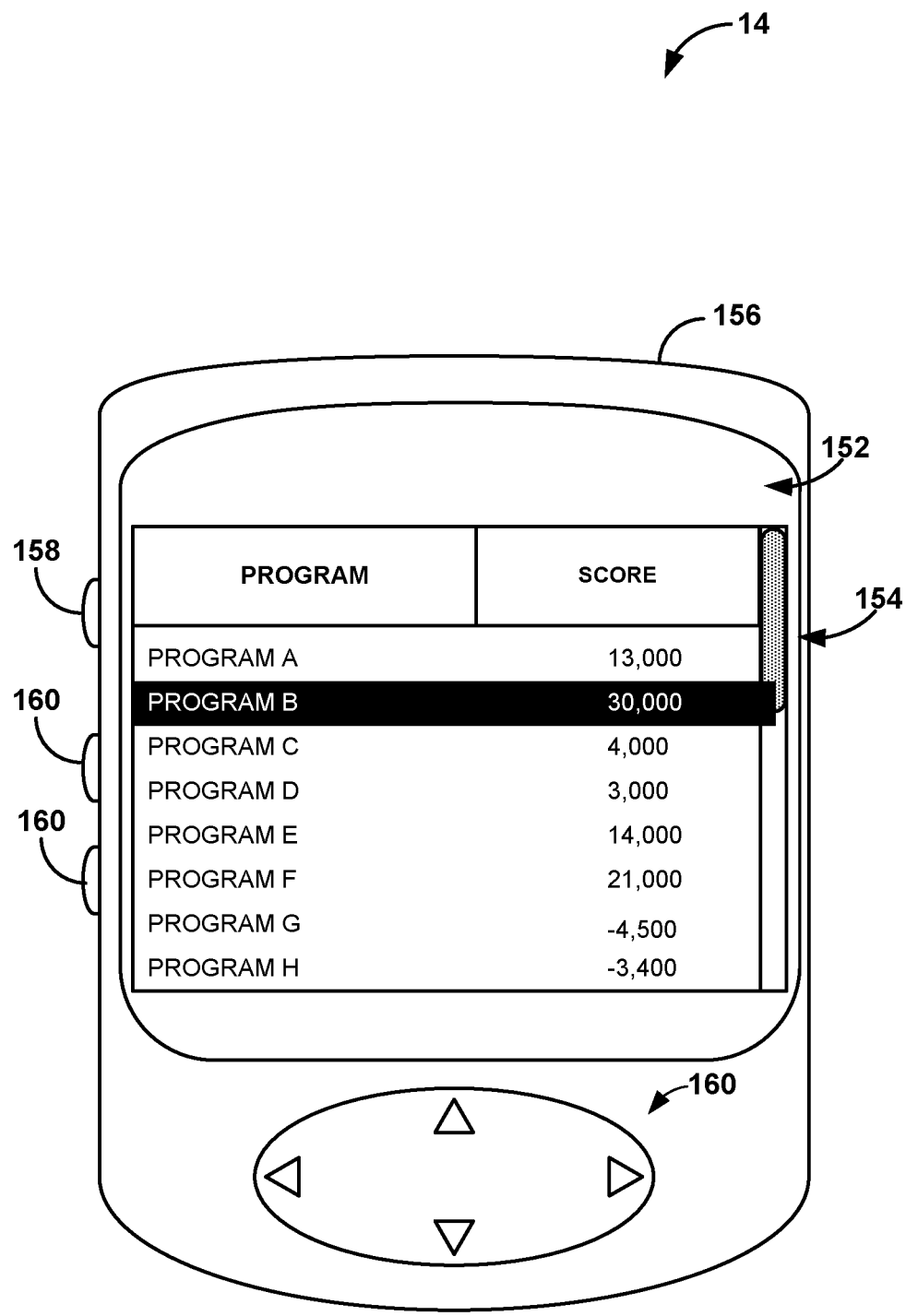
FIG. 8 is a schematic illustration of a medical device programmer, which includes a display presenting a graphical user interface (GUI) with a list of therapy programs.

In the example shown in FIG. 8, programmer 14 also includes housing 156, power button 158, and various other buttons 160 that may be used to provide input to programmer 14, control the functions of programmer 14, and the like. Housing 152 may substantially enclose the components of programmer 14, such as processor 80 and memory 82. A user may depress power button 158 to turn programmer 14 on or off. Buttons 160 may allow the user to navigate through items presented on display 152. For example, the clinician may use buttons 160 to move between items presented on display 152 or move to another screen not currently shown by display 152, to navigate between screens of GUI 154, and to scroll through the therapy programs presented by GUI 154. The clinician may select any highlighted element in GUI 154 via one or more of the buttons 160. For example, using buttons 160, the clinician may scroll to and select "PROGRAM B," which is shown to be highlighted in FIG. 8, in order to receive more information about Program B, such as the stimulation parameter values defined by Program B. In other examples, scroll bars, a touch pad, scroll wheel, individual buttons, a stylus (in combination with a touch screen display 154) or a joystick may perform the complete or partial function of one or more buttons 160.

Programmer 14 may take other shapes or sizes not described herein. For example, programmer 14 may take the form of a clam-shell shape, similar to cellular phone designs. In some examples, programmer 14 may be implemented on a smart phone. In any shape, programmer 14 may be capable of performing the functions described herein. Furthermore, in other embodiments, the buttons of programmer 14 may perform different functions than the functions provided in FIG. 8 as an example. In addition, other embodiments of programmer 14 may include different button layouts or number of buttons. For example, display 154 may be a touch screen that incorporates all user interface and user input mechanism functionality.

In examples discussed herein, processor 80 (or a processor of another device, such as IMD 16) may determine the effect of the electrical stimulation delivered by a selected one of electrodes 24, 26 on tissue of patient 12 based on a VTA expected to result from the electrical stimulation delivered by the selected electrode, the electrical stimulation being generated in accordance with a particular set of electrical stimulation parameter values. Processor 80 may determine the VTA by modeling the effects of the electrical stimulation on tissue in order to determine the tissue of the patient that will be activated by the electrical stimulation. In some examples, the VTA is defined by the tissue of patient 12 that will be activated by the electrical stimulation.

Figure 9:
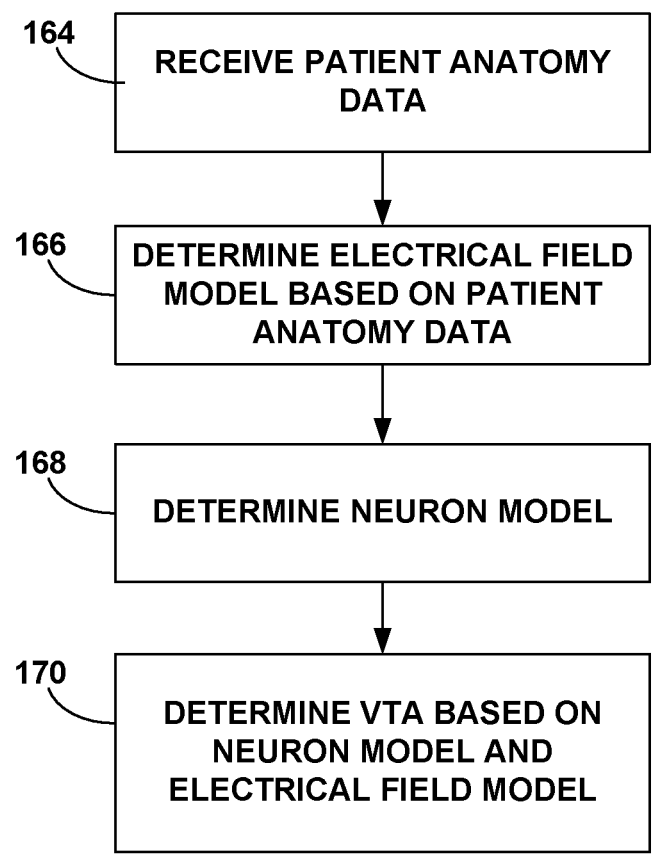
FIG. 9 is a flow diagram illustrating an example technique for determining a volume of tissue activation.

FIG. 9 is a flow diagram of an example technique for determining a VTA. In accordance with the technique shown in FIG. 9, processor 80 receives anatomy data necessary for creating an electrical field model (164). The anatomy data indicates one or more characteristics of tissue proximate to the selected electrode and may be stored, e.g., as anatomy data 92 in memory 82 (FIG. 3). The tissue proximate to the selected electrode may be identified based on the known location of leads 20 within patient 12 or, if leads 20 are not implanted in patient 12, a target location of leads 20. For example, given a patient's MM and post-operative CT scan, processor 80 can determine the position of lead 20 in brain 28 and, therefore, the anatomical structures proximate to the implanted electrodes 24, 26. As another example, given a patient's MM or CT scan, processor 80 can determine the anatomical structures proximate to the target location of electrodes 24, 26 of leads 20, even if leads 20 have not yet been implanted in patient 12.

The patient anatomy data may be specific to or customized for patient 12, or may be more general (e.g., generic physical characteristics of human tissue applicable to a plurality of patients). In some examples, the patient anatomy data includes an anatomical image of a target therapy delivery site within patient 12, a reference anatomical image, which may not be specific to patient 12, an anatomical atlas indicating specific structures of the patient's anatomy or a map of the tissue characteristics (e.g., conductivity or density) adjacent to electrodes 24, 26 of leads 20. The patient anatomy data may be created based on data generated by medical imaging, such as, but not limited to, CT, MM, or any other volumetric imaging system. Processor 60 may store the patient anatomy data within section 92 of memory 82 (FIG. 3).

Processor 80 may model the effect of the electrical stimulation delivered by the selected electrode on tissue of patient 12. In the example shown in FIG. 9, processor 80 determines an electrical field model based on patient anatomy data (166). The electrical field model indicates the electrical field that will propagate away from the electrode when an electrical stimulation signal defined by the set of electrical stimulation parameter values is delivered by the electrode. In some cases, this determining of the electrical field model may involve retrieving the model from memory. In other cases, processor 80 may, for example, implement an algorithm (e.g., stored as a VTA algorithm 96 in memory 82 of programmer 14) to determine the electrical field model. The algorithm may take the received patient anatomy data into consideration, along with electrical field model equations that define electrical current propagation in order to determine how the electrical current will propagate away from the selected electrode.

Tissue variation within brain 28 (or other site within patient 12) may change the electrical current propagation from the electrode in some directions. These variations may contribute to varying therapeutic windows of electrodes 24, 26 of leads 20. Thus, the electrical field model equations take into consideration the actual or expected physical tissue characteristics (e.g., tissue impedance characteristics) of the tissue adjacent electrodes 24, 26 of leads 20, which is included in the anatomy data 92, which may be patient-specific in some examples. From the electrical field model equations, processor 80 may estimate an electrical field that will be produced in therapy delivery via the selected electrode when IMD 16 generates an electrical stimulation signal in accordance with the set of electrical stimulation parameter values.

The expected physical tissue characteristics may be based on a standard electrical field model that employs standard tissue characteristics for various types of tissues rather than determining an electrical field model that is based on patient-specific anatomy data. In such examples, processor 80 may determine the characteristics (e.g., size, shape, and power distribution) of the electrical field based on generic physical characteristics of human tissue and known physical characteristics of the electrodes 24, 26 of leads 20. The actual physical tissue characteristics may be based on patient-specific data. In such examples, processor 80 may determine the characteristics of the electrical field based on the actual anatomical structure of patient 12 being treated. While in either example of using a patient-specific or more generic electrical field model, the electrical field model may be an approximation of what the electrical field would be in brain 28 of a specific patient 12, the electrical field model determined based on the actual anatomical structure of patient 12 may be a more accurate representation of the electrical field that will result from the delivery of electrical stimulation via the selected electrode.

In the technique shown in FIG. 9, processor 80 determines a neuron model (168). The neuron model indicates, for each of a plurality of volumes of tissue of patient 12, the voltage or current amplitude that is required for the tissue to be stimulated. For example, the neuron model may be a 3D grid of voxels, and each voxel may be associated with a voltage or current amplitude that is required for tissue within the particular voxel to be stimulated. As another example, the neuron model may include a grid of two-dimensional (2D) areas, where each area of the grid may be associated with a voltage or current amplitude that is required for tissue within the particular area to be stimulated. In some examples, the neuron model is predetermined by another processor or using some other technique, and stored by memory 82 of programmer 14 (or another memory of another device); processor 80 may determine the neuron model by retrieving it from the memory.

Processor 80 determines a VTA based on the electrical field model and the neuron model (170). The VTA may indicate which tissue of patient 12 will be activated (e.g., stimulated) by the electrical field expected to be generated from the delivery of electrical stimulation. In some examples, processor 80 determines the VTA by at least applying the neuron model to the electrical field determined by the electrical field model. The neuron model will indicate which neurons will be activated by the electrical field. The electrical field expected to result from delivery of electrical stimulation by the selected electrode and according to a particular set of electrical stimulation parameters may have an intensity too low to activate the neurons in at least some tissue proximate to the selected electrode. Thus, by applying the neuron model to the electrical field determined by the electrical field model, processor 80 may determine the volume of tissue that is expected to be activated if electrical stimulation is delivered by the selected electrode to a target tissue location with specified electrical stimulation parameter values.

As discussed above, in some examples, processor 80 is configured to generate a VTA using an electrical field model that indicates tissue conductance that is not specific to patient 12, but, rather, is a general model that may be used to estimate the VTA for a general population of patients. Tissue conductance, however, may vary from patient to patient. In some examples, processor 80 (or another processor) is configured to generate a VTA that is more specific to patient 12, while still using a general model.

Figure 10:
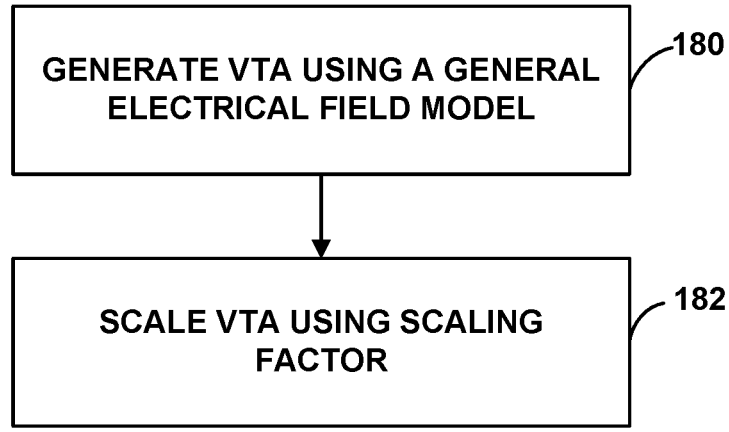
FIG. 10 is a flow diagram illustrating an example technique for determining a patient-specific volume of tissue activation.

For example, as shown in the technique of FIG. 10, processor 80 may generate a VTA using an electrical field model (180) that is not patient-specific and then scale the VTA using a scaling factor that was determined using actual patient responses to electrical stimulation therapy (182).

Thus, the scaling factor may be specific to patient physiology. Processor 80 may, for example, increase the volume of the VTA by the scaling factor for patients that have tissue having a relatively lower impedance than the tissue impedance indicated by the general (or generic) electrical field model. As another example, processor 80 may decrease the volume of the VTA by the scaling factor for patients that have tissue having a higher impedance than the tissue impedance indicated by the general electrical field model. The VTA scaled using the scaling factor may better represent a patient-specific prediction of the effects of electrical stimulation than a VTA generated using only the general electrical field model.

Processor 80 (or another processor) may determine the scaling factor using sensed data that indicates actual responses of patient 12 to electrical stimulation therapy. The sensed data may indicate, for example, how the electrical stimulation propagated through tissue of patient 12, as compared to the general electrical field model. The scaling factor may help quantify this difference. IMD 16 and leads 20 are configured such that stimulation generator 64 may generate and deliver electrical stimulation via one electrode in a unipolar configuration or using multiple electrodes, and sensing module 66 may sense using other electrodes of leads 24, 26. For example, sensing module 66 may sense differential voltages via two or more of the other electrodes. This may allow IMD 16 to stimulate tissue and simultaneously record the voltage potentials along one or both leads 20, where the voltage potentials may indicate the actual effects of the electrical stimulation on tissue of a specific patient 12. In this way, the sensed data may help generate VTAs that more accurately estimate the extent to which electrical stimulation delivered according to a particular therapy program may activate tissue of patient 12.

Figure 11:
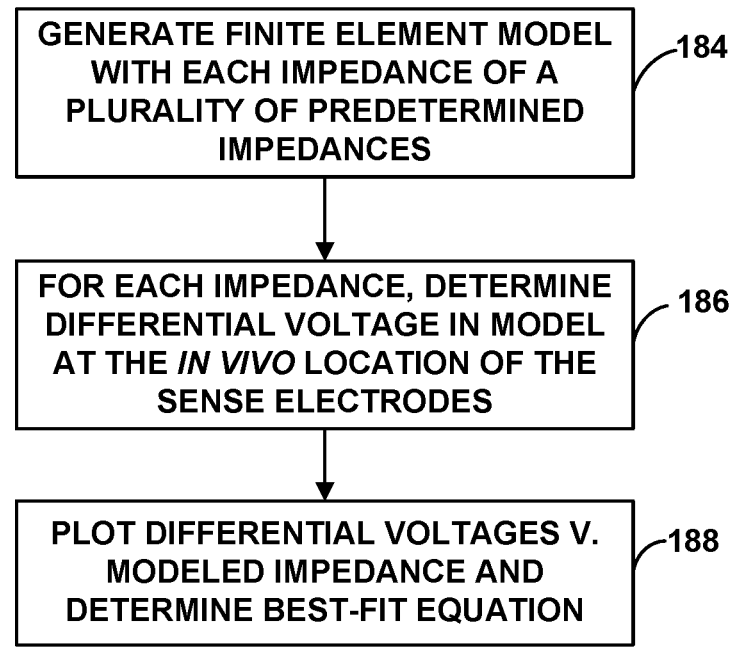
FIG. 11 is a flow diagram of an example technique for determining the relationship between sensed voltage differentials and tissue impedance values for a general electrical field model.

In some examples, a relationship between sensed voltage differentials and tissue impedance values for the general electrical field model may be determined to help determine a sensing scaling factor. Impedance values discussed herein may refer to any suitable value indicative of electrical impedance, such as a resistance value, a reactance value, a complex impedance value that includes a resistance component and a reactance component, or the like. FIG. 11 is a flow diagram of an example technique for determining the relationship between sensed voltage differentials and tissue impedance values for the general electrical field model.

In the technique shown in FIG. 11, processor 80 generates, for each impedance value (referred to generally as "$Z_{model}$") of a plurality of impedance values, a finite element method model that indicates the electrical properties of the tissue of the general electrical field model (184). The plurality of impedance values can be, for example, each impedance value between 500 ohms and 2000 ohms in 100 ohm increments. Other impedance values can also be used in other examples.

For each finite element model, processor 80 determines the differential voltage at the location of the electrical field model corresponding to the in vivo implant site of electrodes 24, electrodes 26, or both electrodes 24, 26 in patient 12 during the modeled delivery of electrical stimulation according to a particular therapy program (186). Because the finite element model indicates tissue conductance properties of the general electrical field model, processor 80 may solve for the extracellular voltage within the tissue (e.g., the brain) using the finite element model by at least determining the voltage sensed via a first electrode and the voltage sensed via a second electrode during the delivery of electrical stimulation via a third electrode, and then subtracting the sensed voltages to determine the differential voltage. For example, as described with respect to FIG. 9, processor 80 may determine, using an electrical field modeling algorithm stored by memory 82, an electrical field model that indicates the electrical field that will propagate away from the electrode when an electrical stimulation signal defined by the particular therapy program is delivered by the third electrode. This electrical field modeling algorithm may include electrical field model equations that indicate general (not specific to patient 12) tissue characteristics of tissue at a location of corresponding to the location of implanted electrodes 24, 26 of leads 20.

In order to determine the voltages sensed via the first and second electrodes, processor 80 may determine the voltage amplitudes of the electrical field at a particular location based on the electrical field model. The particular location can be, for example, a specific distance from the third (stimulating) electrode, such as a relative distance between a sense electrode and the stimulation location. For example, to determine the voltage sensed via the first electrode, the distance may be the distance between the first electrode and third electrode (e.g., as measured between the centers of the electrodes, along a longitudinal distance of the lead, or as measured as the shortest distance between the electrodes). Similarly, to determine the voltage sensed via the first electrode, the distance may be the distance between the second electrode and third electrode.

Processor 80 may generate a plot of the differential voltage versus modeled impedance, and determine a best fit equation (188) that represents the relationship between the model impedance values and differential voltages for the particular therapy program. Processor 80 may store the best fit equation in memory 82, e.g., as a montage equation associated with the particular therapy program.

Figure 12:
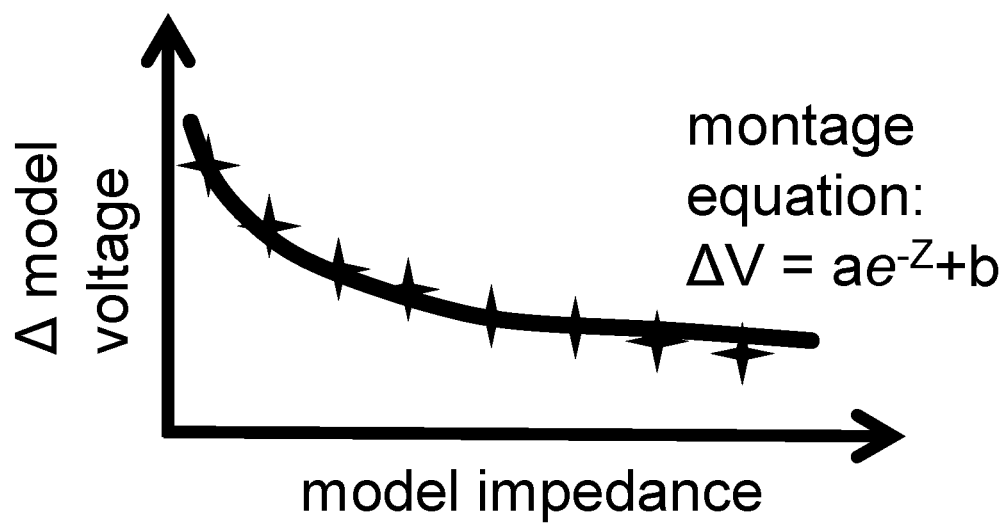
FIG. 12 is a conceptual illustration of an example plot that illustrates the relationship between model impedance values ($Z_{model}$) and model differential voltages.

FIG. 12 is a conceptual illustration of an example plot that illustrates the relationship between the model impedance values ($Z_{model}$) and the model differential voltages. In the example shown in FIG. 12, the montage equation is a quadratic equation, which results in a regression curve. In other examples, other best fit equations may be used to define the relationship between the model impedance values ($Z_{model}$) and the model differential voltages.

In some examples, processor 80 may repeat the technique shown in FIG. 11 for each therapy program of a stored set of therapy programs. Because the VTA may change for a particular therapy program based on the selected electrode combination as well as the impedance value, repeating the technique shown in FIG. 11 for a plurality of therapy programs may help better compare the efficacy of a particular therapy program.

In some examples, the stored set of therapy programs may include one or more therapy programs for each unipolar electrode combination of a plurality of unipolar electrode combinations. The plurality of unipolar electrode combinations can be, for example, the unipolar electrode combinations defined by each electrode 24 of lead 20A, each electrode 26 of lead 20B, or each electrode 24, 26 of both leads 20. In addition, the plurality of therapy programs may include multiple therapy programs for each unipolar electrode combination, e.g., whereby the programs with the same electrode combination may differ from each other based on their stimulation amplitudes, pulse widths, stimulation frequencies, or another therapy parameters or combination of therapy parameters.

In some examples, the plurality of therapy programs may include, for each electrode combination, therapy programs having a plurality of voltage amplitudes (e.g., in certain increments) in a range of voltage amplitudes and therapy programs having a plurality of pulse widths (e.g., in certain increments) in a range of pulse widths. This variety of therapy parameter information may be used by processor 80 to generate best fit equations for a plurality of different therapy programs. For example, the plurality of therapy programs may include, for each of a plurality of unipolar electrode combinations, at least one therapy program for each stimulation amplitude value between 0.3 volts to 10 volts in 0.1 volt increments, and at least one therapy program for each of the following pulse widths: 60 microseconds (μs), 90 μs, 150 μs, 210 μs, 330 μs, and 450 μs.

Figure 13:
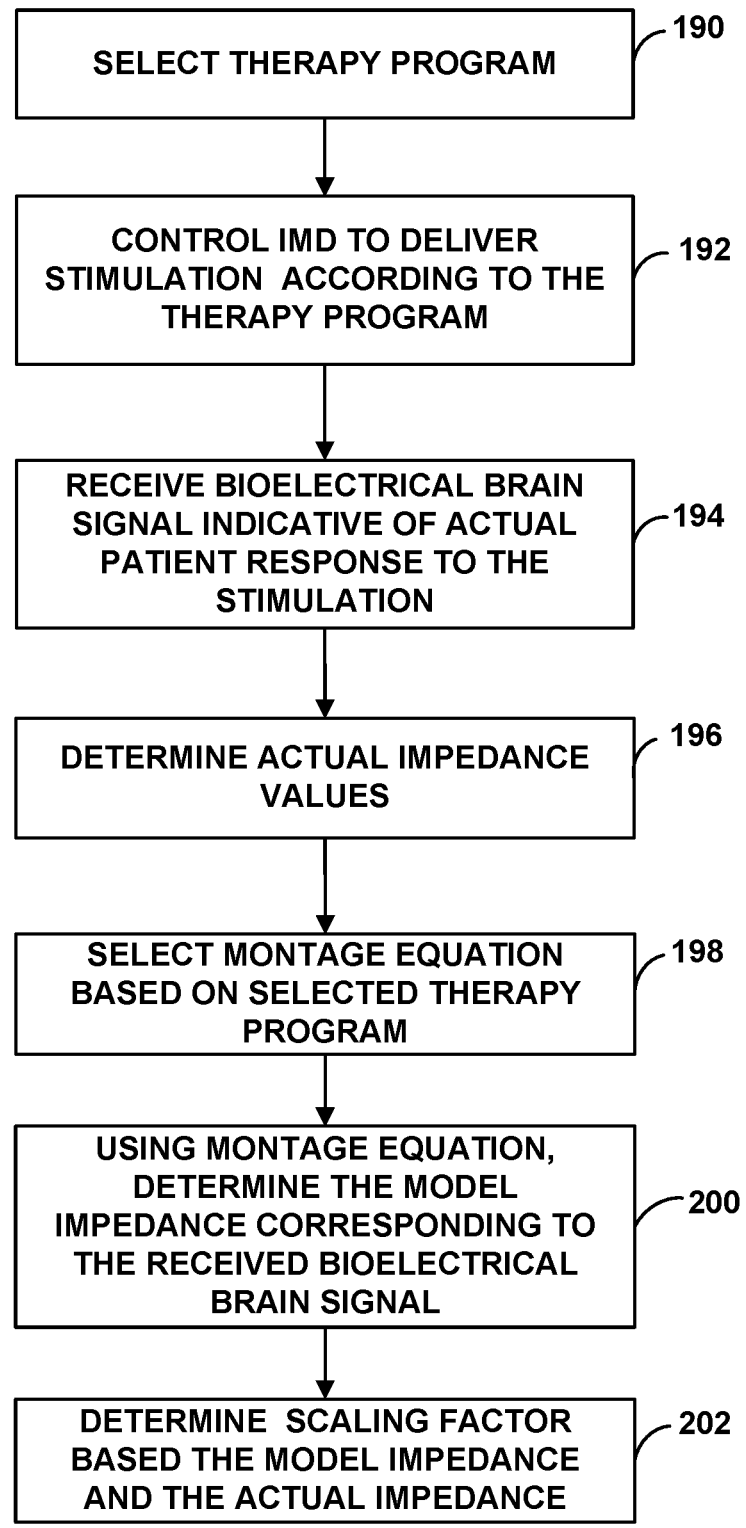
FIG. 13 is a flow diagram of an example technique for determining a scaling factor for generating a patient-specific VTA.

After the best fit equations are determined for a plurality of therapy programs, processor 80 may determine a scaling factor for a particular therapy program and a particular patient 12. Processor 80 may apply the scaling factor to a VTA generated based on general electrical field model to better simulate the actual patient response to electrical stimulation therapy according to the therapy program. FIG. 13 is a flow diagram of an example technique for determining a scaling factor. Processor 80 selects a therapy program from a plurality of stored therapy programs (190), and controls IMD 16 to deliver, to patient 12, electrical stimulation according to the selected therapy program (192). For example, processor 80 may transmit a control signal to IMD 16 via the respective telemetry modules 84, 70 that causes processor 60 (FIG. 2) of IMD 16 to control stimulation generator 64 (FIG. 2) to generate and deliver the electrical stimulation. In other examples, a clinician may control IMD 16 to deliver, to patient 12, electrical stimulation according to the selected therapy program.

Processor 80 also controls IMD 16 to sense an electrical signal during the delivery of electrical stimulation at the selected amplitude via the selected electrode, the electrical signal indicating the actual response of the tissue of patient 12 to the electrical stimulation therapy. For example, processor 80 may transmit a control signal to IMD 16 via the respective telemetry modules 84, 70 that causes processor 60 (FIG. 2) of IMD 16 to control sensing module 66 (FIG. 2) to sense the signal at the same time stimulation generator 64 is delivering electrical stimulation to patient 12. Sensing module 66 may sense the signal with different electrodes than the electrode used to deliver the electrical stimulation. The electrodes with which IMD 16 senses the voltage or other parameter can be, for example, directly adjacent to (e.g., on either side of) the electrode selected for delivering the stimulation.

Processor 80 receives, from IMD 16, the sensed bioelectrical signal indicative of actual patient response to the electrical stimulation (194). In addition, processor 80 determines the actual impedance value ($Z_{clinical}$) for the one or more electrodes 24, 26 used to deliver the electrical stimulation to patient 12 (196). Each electrode 24, 26 may be coupled to a respective insulated conductor within the respective lead 20. An electrode, associated conductor, and tissue of patient 12 proximate to the electrode may form an electrical path and, for a particular electrode 24, 26, processor 80 may determine the actual impedance ($Z_{clinical}$) of the electrical path. Processor 80 of programmer 14 of processor 60 of IMD 16 may use any suitable technique to determine the actual impedance value, which can be determining an electrical parameter value indicative of the impedance. In some examples, processor 60 of IMD 16 (e.g., in response to a control signal from processor 80) may control IMD 16 to perform an impedance measurement by delivering, from stimulation generator 64, an electrical signal having a constant voltage between at least two electrodes 24, 26, and measuring a resulting current of the signal that is sensed by two or more electrodes. Processor 60 may determine a resistance based upon the voltage amplitude of the electrical signal and the measured amplitude of the resulting current. The current of the sensed signal or the determined resistance may be electrical parameter values indicative of the impedance of the electrical path comprising the electrodes.

In other examples, processor 60 of IMD 16 may perform impedance measurement by controlling stimulation generator 64 to deliver a current pulse across at least two electrodes 24, 26, and measuring a resulting voltage of a signal that is sensed by two or more electrodes 24, 26. Processor 60 may determine a resistance based upon the current amplitude of the pulse and the measured amplitude of the resulting voltage. The voltage of the sensed signal or the determined resistance may be electrical parameter values indicative of the impedance path comprising the electrodes.

In either example, processor 60 may transmit to processor 80 the electrical parameter value indicative of the impedance, and processor 80 may use the electrical parameter value as the actual impedance value ($Z_{clinical}$).

Processor 80 selects, from memory 82, a montage equation that corresponds to the selected therapy program (198), the montage equation indicating the relationship between the modeled differential voltages and model impedance values ($Z_{model}$) for the general electrical field model. A technique for determining the montage equation is discussed above with respect to FIG. 11. Based on the selected montage equation, processor 80 determines which model impedance value substantially corresponds (corresponds exactly or nearly exactly) to the voltage of the sensed bioelectrical brain signal indicative of the actual patient response to the electrical stimulation according to the selected therapy program (200). For example, using the montage equation with the known variable being the differential voltage, processor 80 may solve for the model impedance ($Z_{model}$).

Processor 80 may then determine the scaling factor based on the model impedance ($Z_{model}$) and the actual impedance value ($Z_{clinical}$) (202). In some examples, processor 80 determines the scaling factor as the ratio between the model impedance value and the actual impedance value. That is, in some examples, the scaling factor is $Z_{model}/Z_{clinical}$. In this way, the scaling factor may be determined based on an equation that indicates the relationship between the modeled response and the actual patient response.

In other examples, processor 80 may determine a scaling factor based on additional or different physiological parameters, different model dependencies, or both. For example, in some examples, processor 80 may determine a montage equation that indicates the relationship between a particular power level in a frequency band of a sensed bioelectrical signal and the differential voltage. The one or more selected physiological parameters may differ between the general electrical field model and the actual patient tissue, such that the relationship between a modeled physiological parameter value and an actual physiological parameter value may be used to scale a VTA to more accurately resemble the stimulation spread occurring within tissue of patient 12 during the delivery of electrical stimulation.

In some cases, the conductivity of tissue of patient 12 proximate implanted electrodes 24, 26 may change over time. As a result, the actual volume of tissue activated by a particular therapy program implemented by IMD 16 may change over time. A change in the actual volume of tissue activated may affect the efficacy of the therapy program because the tissue of a particular region of interest (e.g., a particular brain structure) may no longer be receiving the desired level of electrical stimulation or tissue in a region associated with adverse effects may unintentionally be receiving electrical stimulation. In some examples, processor 60 of IMD 16, processor 80 of programmer 14, or a processor of another device may periodically determine a scaling factor using the techniques described above, e.g., the technique shown in FIG. 13, to update the stimulation parameter values (e.g., in a closed loop or pseudo-closed loop manner) with which IMD 16 generates and delivers electrical stimulation to patient 12 in order to compensate for a change in the actual VTA.

For example, after IMD 16 and leads 20 are implanted in patient 12, processor 80 may determine the scaling factors for each therapy program of a plurality of therapy programs stored by memory 62 of IMD 16. These scaling factors may be associated with the respective therapy programs and may be stored by memory 62 of IMD 16 or a memory of another device, such as programmer 14. The stored scaling factors may be referred to as baseline scaling factors. Sometime after IMD 16 and leads 20 are implanted in patient 12, e.g., after a period of days, weeks, or even months, processor 60 may redetermine a scaling factor for a therapy program being implemented by IMD 16 for therapy delivery to patient 12, e.g., using the technique shown in FIG. 13. Processor 60 may then determine the change in the scaling factor for that therapy program, relative to the baseline scaling factor associated with the therapy program. Processor 60 may then adjust the stimulation parameter values (e.g., the stimulation voltage or the pulse width, or both) based on the determined change and then control stimulation generator 64 (FIG. 2) to deliver electrical stimulation to patient 12 in accordance with the adjusted stimulation parameter values. For example, processor 60 may determine the ratio between the determined scaling factor and the baseline scaling factor and adjust one or more stimulation parameter values of the therapy program by the ratio to generate an updated therapy program.

The scaling factor determined for patient 12 may be stored and associated with the patient, e.g., either on paper or electronically. A clinician may review stored scaling factors, generated over time, to better understand how the patient's scaling factor is changing the electrical stimulation therapy over time. In some cases, the change in the scaling factor for a particular patient 12 over time may help the clinician understand and quantify the progression of the patient's condition. In addition, in some cases, the change in the scaling factor for a particular patient 12 over time may help predict, e.g., when power source 72 (FIG. 2) of IMD 16 or another component of therapy system 10 may need to be replaced or otherwise maintained.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
    determining, by one or more processors, a volume of tissue activation (VTA) expected to result from delivery of electrical stimulation by a medical device according to a therapy program;
    registering, by the one or more processors, the VTA to a three-dimensional grid;
    obtaining, by the one or more processors, a representation of a bioelectrical brain signal of a patient sensed during delivery of the electrical stimulation to the patient by the medical device according to the therapy program;
    determining, by the one or more processors, a frequency domain characteristic of the bioelectrical brain signal of the patient;
    determining, by the one or more processors, values for voxels of the three-dimensional grid overlapping with the VTA based on the frequency domain characteristic of the bioelectrical brain signal; and
    controlling, based on the determined values, subsequent delivery of electrical stimulation to the patient.

2. The method of claim 1, further comprising:
    evaluating, based on the values of the voxels, therapy programs of a plurality of therapy programs.

3. The method of claim 2, further comprising:
    presenting, via a user interface, results of the evaluating.

4. The method of claim 3, wherein the results include an indication of a recommended therapy program of the plurality of therapy programs.

5. The method of claim 2, wherein each therapy program of the plurality of therapy programs has a same electrode combination.

6. The method of claim 1, wherein:
determining the VTA expected to result from delivery of electrical stimulation by the medical device according to the therapy program comprises determining, for each respective therapy program of a plurality of therapy programs, a respective VTA expected to result from delivery of electrical stimulation by the medical device according to the respective therapy program;
registering the VTA comprises registering each of the respective VTAs to the three-dimensional grid;
obtaining the representation of the bioelectrical brain signal comprises obtaining, for each respectively therapy program, a respective representation of a bioelectrical brain signal of the patient sensed during delivery of electrical stimulation to the patient by the medical device according to the respective therapy program;
determining the frequency domain characteristic comprises determining, for each respective therapy program, a frequency domain characteristic of the respective bioelectrical brain signal of the patient; and
determining the values for the voxels comprises determining values for voxels overlapping with the respective VTAs based on the frequency domain characteristic of the respective bioelectrical brain signal.

7. The method of claim 6, further comprising:
determining, for each respective therapy program, a respective score based on the values of the voxels that overlap with the respective VTA.

8. The method of claim 7, further comprising:
presenting, via a user interface, a list comprising the plurality of therapy programs and respective scores; and
ordering the plurality of therapy programs within the list based on the scores.

9. A system comprising:
a memory;
a user interface; and
one or more processors that are implemented in circuitry, operably coupled to the memory, and configured to:
determine a volume of tissue activation (VTA) expected to result from delivery of electrical stimulation by a medical device according to a therapy program;
obtain a representation of a bioelectrical brain signal of a patient sensed during delivery of the electrical stimulation to the patient by the medical device according to the therapy program;
register the VTA to a three-dimensional grid;
determine a frequency domain characteristic of the bioelectrical brain signal of the patient;
determine values for voxels of the three-dimensional grid overlapping with the VTA based on the frequency domain characteristic of the bioelectrical brain signal; and
evaluate, based on the values of the voxels, therapy programs of a plurality of therapy programs; and
present, via the user interface, results of the evaluating.

10. The system of claim 9, wherein the plurality of therapy programs includes the therapy program.

11. The system of claim 10, wherein each therapy program of the plurality of therapy programs has a same electrode combination.

12. The system of claim 10, wherein:
to determine the VTA expected to result from delivery of electrical stimulation by the medical device according to the therapy program, the one or more processors are configured to determine, for each respective therapy program of a plurality of therapy programs, a respective VTA expected to result from delivery of electrical stimulation by the medical device according to the respective therapy program;
to register the VTA, the one or more processors are configured to register each of the respective VTAs to the three-dimensional grid;
to obtain the representation of the bioelectrical brain signal, the one or more processors are configured to obtain, for each respectively therapy program, a respective representation of a bioelectrical brain signal of the patient sensed during delivery of electrical stimulation to the patient by the medical device according to the respective therapy program;
to determine the frequency domain characteristic, the one or more processors are configured to determine, for each respective therapy program, a frequency domain characteristic of the respective bioelectrical brain signal of the patient; and
to determine the values for the voxels, the one or more processors are configured to determine values for voxels overlapping with the respective VTAs based on the frequency domain characteristic of the respective bioelectrical brain signal.

13. The system of claim 12, wherein the one or more processors are further configured to:
determine, for each respective therapy program, a respective score based on the values of the voxels that overlap with the respective VTA.

14. The system of claim 13, further comprising:
the user interface, wherein the one or more processors are further configured to present, via the user interface, a list comprising the plurality of therapy programs and the scores, and order the plurality of therapy programs within the list based on the scores.

15. The system of claim 10, wherein the system includes the medical device.

16. The system of claim 9, wherein the results include an indication of a recommended therapy program of the plurality of therapy programs.

17. A non-transitory computer-readable storage medium storing instructions that, when executed, cause one or more processors to:
determine a volume of tissue activation (VTA) expected to result from delivery of electrical stimulation by a medical device according to a therapy program;
register the VTA to a three-dimensional grid;
obtain a representation of a bioelectrical brain signal of a patient sensed during delivery of the electrical stimulation to the patient by the medical device according to the therapy program;
determine a frequency domain characteristic of the bioelectrical brain signal of the patient sensed during delivery of the electrical stimulation to the patient by the medical device according to the therapy program;
determine values for voxels of the three-dimensional grid overlapping with the VTA based on the frequency domain characteristic of the bioelectrical brain signal; and
control, based on the determined values, subsequent delivery of electrical stimulation to the patient.

18. The non-transitory computer-readable storage medium of claim 17, further storing instructions that cause the one or more processors to evaluate, based on the values of the voxels, therapy programs of a plurality of therapy programs, wherein the plurality of therapy programs includes the therapy program.

19. The non-transitory computer-readable storage medium of claim 18, further storing instructions that cause the one or more processors to output, for display via a user interface, results of the evaluation.

* * * * *